(12) United States Patent
Hooyberghs et al.

(10) Patent No.: US 10,807,960 B2
(45) Date of Patent: Oct. 20, 2020

(54) COMPOUNDS, COMPOSITIONS, AND METHODS FOR CONTROLLING BIOFILMS

(71) Applicant: KATHOLIEKE UNIVERSITEIT LEUVEN, Leuven (BE)

(72) Inventors: Geert Hooyberghs, Westerlo (BE); Stijn Robijns, Aarschot (BE); Hans Steenackers, Leuven (BE); Erik Van Der Eycken, Ninove (BE)

(73) Assignee: Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 15/770,968

(22) PCT Filed: Oct. 27, 2016

(86) PCT No.: PCT/BE2016/000049
§ 371 (c)(1),
(2) Date: Apr. 25, 2018

(87) PCT Pub. No.: WO2017/070755
PCT Pub. Date: May 4, 2017

(65) Prior Publication Data
US 2018/0305321 A1    Oct. 25, 2018

(30) Foreign Application Priority Data
Oct. 27, 2015  (GB) .................................. 1518988.9

(51) Int. Cl.
*C07D 233/88*  (2006.01)
*A61P 31/04*  (2006.01)

(52) U.S. Cl.
CPC ............ *C07D 233/88* (2013.01); *A61P 31/04* (2018.01)

(58) Field of Classification Search
None
See application file for complete search history.

(56) References Cited

FOREIGN PATENT DOCUMENTS

WO    2011080132 A2    7/2011

OTHER PUBLICATIONS

Bjarnsholt et al., "Interference of Pseudomonas aeruginosa signalling and biofilm formation for infection control", Expert Rev Mol Med, 2010, 12:e11, doi:10.1017/S1462399410001420.
Landini et al., "Molecular mechanisms of compounds affecting bacterial biofilm formation and dispersal", Appl Microbiol Biotechnol, 2010, 86:813-823.
Lynch et al., "New antibiotic agents and approaches to treat biofilm-associated infections", Expert Opin Ther Pat, 2010, 20:1373-1387.
Ren et al., "Differential gene expression for investigation of *Escherichia coli* biofilm inhibition by plant extract ursolic acid", Appl Environ Microbiol, 2005, 71:4022-4034.
(Continued)

*Primary Examiner* — Anna Pagonakis
(74) *Attorney, Agent, or Firm* — Dinsmore & Shohl, LLP

(57) ABSTRACT

The present invention relates to substituted 5-aryl-2-aminoimidiazole compounds being active against microbial biofilm formation. The invention also relates to compositions comprising a microbial biofilm inhibiting amount of said substituted 5-aryl-2-aminoimidazole compounds in combination with excipients. Methods for inhibiting or controlling microbial biofilm formation in a plant, a body part of a human or an animal, or a surface with which a human or an animal may come into contact are also disclosed.

8 Claims, 12 Drawing Sheets

1

2

3

4

5

6

(56) References Cited

OTHER PUBLICATIONS

Rogers et al., "A 2-aminobenzimidazole that inhibits and disperses gram-positive biofilms through a zinc-dependent mechanism", Journal of the American Chemical Society, 2009, 131:9868-9869.
Steenackers et al., "Structure Activity Relationship of 4(5)-Phenyl-2-amino-1H-imidazoles, N1-Substituted 2-Aminoimidazoles and Imidazo[1,2-a]pyrimidinium Salts as Inhibitors of the Biofilm Formation by *Salmonella typhimurium* and Pseudomonas aeruginosa", Journal of Medicinal Chemistry, 2011 54:472-482.
Steenackers et al., "Structure-activity relationship of 2-hydroxy-2-aryl-2,3-dihydro-imidazo[1,2-a]pyrimidinium salts and 2N-substituted 4(5)-aryl-2-amino-1H-imidazoles as inhibitors of biofilm formation by *Salmonella typhimurium* and Pseudomonas aeruginosa", Bioorg Med Chem, 2011, 19:3462-3473.
Ermolat'Ev et al., "Concise and diversity-oriented route toward polysubstituted 2-aminoimidazole alkaloids and their analogues", Angew Chem Int Ed Engl, 2010, 49:9465-9468.
Steenackers et al., "Microwave-Assisted One-Pot Synthesis and Anti-Biofilm Activity of 2-Amino-1H-imidazole/Triazole Conjugates", Organic and Biomolecular Chemistry Submitted, 2013, 12:3671-3678.
Folkesson et al., "Adaptation of Pseudomonas aeruginosa to the cystic fibrosis airway: an evolutionary perspective", Nat Rev Microbiol, 2012, 10:841-851.
Guo et al., "One-Pot Three-Component Strategy for Functionalized 2-Aminoimidazoles via Ring Opening of α-Nitro Epoxides", Organic letters, 2015, 17:1157-1159.
Ermolat'Ev et al., "Efficient one-pot, two-step, microwave-assisted procedure for the synthesis of polysubstituted 2-aminoimidazoles", Organic letters, 2006, 8:5781-5784.
Ribeiro et al., "Infection of orthopedic implants with emphasis on bacterial adhesion process and techniques used in studying bacterial-material interactions", Biomatter, 2012, 2:176-194.
Giles et al., "Addition-Hydroamination Reactions of Propargyl Cyanamides: Rapid Access to Highly Substituted 2-Aminoimidazoles", Angewandte Chemie (International ed in English), 2009, 121:3162-3166.
Liberati et al., "An ordered, nonredundant library of Pseudomonas aeruginosa strain PA14 transposon insertion mutants", Proc Natl Acad Sci U S A, 2006, 103:2833-2838.
Iwase et al., *Staphylococcus epidermidis* Esp inhibits *Staphylococcus aureus* biofilm formation and nasal colonization. Nature, 2010, 465:346-349.
Blattner et al., "The Complete Genome Sequence of *Escherichia coli* K-12", Science, 1997, 277:1453-1462.
Fields et al., "Mutants of *Salmonella typhimurium* that cannot survive within the macrophage are avirulent", Proc Natl Acad Sci U S A, 1986, 83:5189-5193.
Andersen et al. "gfp-based N-acyl homoserine-lactone sensor systems for detection of bacterial communication", Appl Environ Microbiol, 2001, 67:575-585.
Palleroni et al., "*Pseudomonas cepacia* sp. nov., nom. rev", International Journal of Systematic Bacteriology, 1981, 31:479-481.
Fonzi et al., "Isogenic Strain Construction and Gene Mapping in Candida albicans", Genetics, 1993, 134:717-728.
O'Neill, AJ. "*Staphylococcus aureus* SH1000 and 8325-4: comparative genome sequences of key laboratory strains in staphylococcal research", Lett Appl Microbiol, 2010, 51:358-361.
Horsburgh et al., "B Modulates Virulence Determinant Expression and Stress Resistance: Characterization of a Functional rsbU Strain Derived from *Staphylococcus aureus* 8325-4", Journal of Bacteriology, 2002, 184:5457-5467.
Delattin et al. "Repurposing as a means to increase the activity of amphotericin B and caspofungin against Candida albicans biofilms", J Antimicrob Chemother, 2014, 69:1035-1044.
Janssens et al., "Brominated furanones inhibit biofilm formation by *Salmonella enterica serovar Typhimurium*", Appl Environ Microbiol, 2008, 74:6639-6648.

O'Brien et al., "Investigation of the Alamar Blue (resazurin) fluorescent dye for the assessment of mammalian cell cytotoxicity", European Journal of Biochemistry, 2000, 267:5421-5426.
Steenackers et al., "Evaluation of the Toxicity of 5-Aryl-2-Aminoimidazole-Based Biofilm Inhibitors against Eukaryotic Cell Lines, Bone Cells and the Nematode Caenorhabditis elegans", Molecules, 2014, 19:16707-16723.
Robijns et al., "Identification and characterization of 4-[4-(3-phenyl-2-propen-1-yl)-1-piperazinyl]-5H-pyrimido[5,4-b] indole derivatives as *Salmonella* biofilm inhibitors", FEMS Immunol Med Microbiol, 2012, 65:390-394.
Mishra et al., "Evaluation of the antibacterial and antibiofilm activities of novel CRAMP-vancomycin conjugates with diverse linkers", Org Biomol Chem, 2015, 13:7477-7486.
Liebens et al., "Identification and characterization of an anti-pseudomonal dichlorocarbazol derivative displaying anti-biofilm activity", Bioorg Med Chem Lett, 2014, 24:5404-5408.
Bunders et al., "Identification of aryl 2-aminoimidazoles as biofilm inhibitors in Gram-negative bacteria", Bioorg Med Chem Lett, 2010, 20:3797-3800.
Junker et al., "High-throughput screens for small-molecule inhibitors of Pseudomonas aeruginosa biofilm development", Antimicrob Agents Chemother, 2007, 51:3582-3590.
Zeng et al., "Virtual screening for novel quorum sensing inhibitors to eradicate biofilm formation of Pseudomonas aeruginosa", Appl Microbiol Biotechnol, 2008, 79:119-126.
Cao et al., "In vitro activity of baicalein against Candida albicans biofilms", Int J Antimicrob Agents, 2008, 32:73-77.
Yang et al., "Computer-aided identification of recognized drugs as Pseudomonas aeruginosa quorum-sensing inhibitors", Antimicrob Agents Chemother, 2009, 53:2432-2443.
Payne et al., "Tannic acid inhibits *Staphylococcus aureus* surface colonization in an isaA-dependent manner", Infection and Immunity, 2013, 81:496-504.
Hancock et al., "Dietary plant components ellagic acid and tannic acid inhibit *Escherichia coli* biofilm formation", J Med Microbiol, 2010, 59:496-498.
Rogers et al., "Chemical synthesis and biological screening of 2-aminoimidazole-based bacterial and fungal antibiofilm agents", Chembiochem, 2010, 11:396-410.
Steenackers et al., "Structure-activity relationship of 4(5)-aryl-2-amino-1H-imidazoles, N1-substituted 2-aminoimidazoles and imidazo[1,2-a]pyrimidinium salts as inhibitors of biofilm formation by *Salmonella typhimurium* and Pseudomonas aeruginosa", J Med Chem, 2011, 54:472-484.
Tournu et al., "Candida biofilms and the host: models and new concepts for eradication", Int J Microbiol, 2012, 845352.
Burmolle et al., "Interactions in multispecies biofilms: do they actually matter?", Trends Microbiol, 2014, 22:84-91.
Lee et al., "Biofilm development and enhanced stress resistance of a model, mixed-species community biofilm", ISME J, 2014, 8:894-907.
Harriott, MM, "Candida albicans and *Staphylococcus aureus* form polymicrobial biofilms: effects on antimicrobial resistance", Antimicrob Agents Chemother, 2009, 53:3914-3922.
Adam et al, "Mixed species biofilms of Candida albicans and *Staphylococcus epidermidis*", J Med Microbiol, 2002, 51:344-349.
Luppens et al., "Effect of Veillonella parvula on the antimicrobial resistance and gene expression of *Streptococcus rnutans* grown in a dual-species biofilm", Oral microbiology and immunology, 2008, 23:183-189.
Schwering et al., "Multi-species biofilms defined from drinking water microorganisms provide increased protection against chlorine disinfection", Biofouling, 2013, 29:917-928.
Lopes et al., "Antibiotic resistance of mixed biofilms in cystic fibrosis: impact of emerging microorganisms on treatment of infection", Int J Antimicrob Agents, 2012, 40:260-263.
Cavalcanti et al., "Interactions between *Streptococcus oralis*, Actinomyces oris, and Candida albicans in the development of multispecies oral microbial biofilms on salivary pellicle", Mol Oral Microbiol, 2016, doi:10.1111/omi.12154.
Cerqueira et al., "Biofilm formation with mixed cultures of Pseudomonas aeruginosa/*Escherichia coli* on silicone using artificial urine to mimic urinary catheters", Biofouling, 2013, 29:829-840.

(56) References Cited

OTHER PUBLICATIONS

International Search Report and Written Opinion pertaining to PCT/BE2016/000049 dated Jan. 25, 2017.

Peeters et al., "Modulation of the Substitution Pattern of 5-Aryl-2-Aminoimidazoles Allows Fine-Tuning of Their Antibiofilm Activity Spectrum and Toxicity", Antimicrobial Agents and Chemotherapy, vol. 60, No. 11, Nov. 2016, pp. 6483-6497.

Steenackers et al., "Structure-activity relationship of 2-hydroxy-2-aryl-2,3-dihydroimidazo[1,2-a]pyrimidinium salts and 2N-substituted 4(5)-aryl-2-amino-1H-imidazoles as inhibitors of biofilm formation by *Salmonella typhimurium* and Pseudomonas aeruginosa", Bioorganic & Medicinal Chemistry, vol. 19, 2011, pp. 3462-3473.

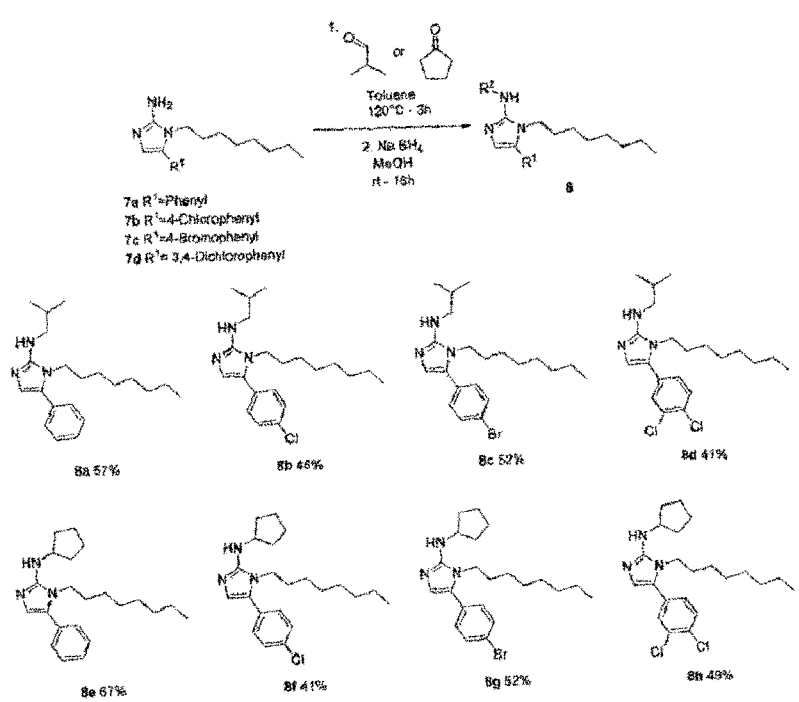

Figure 3A
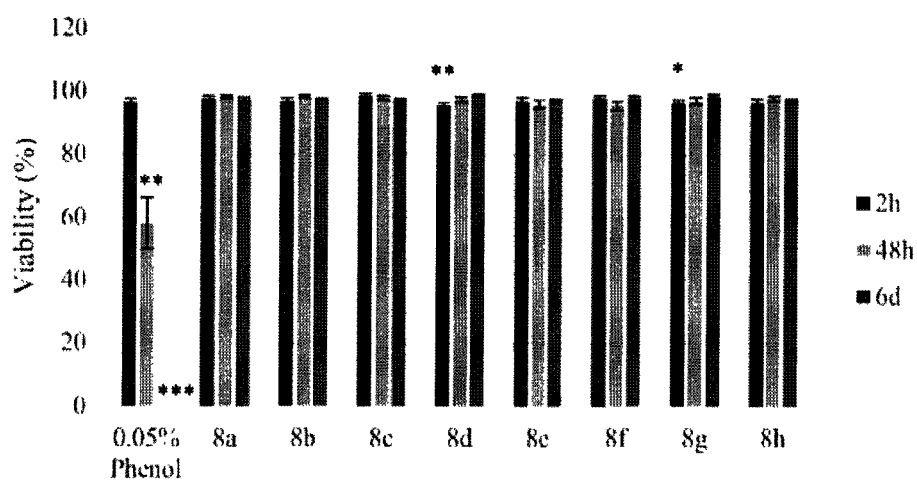
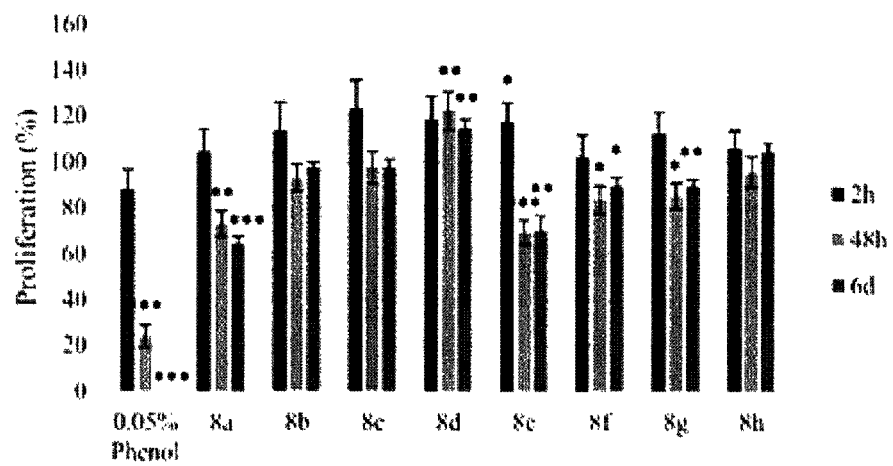

Figure 3B
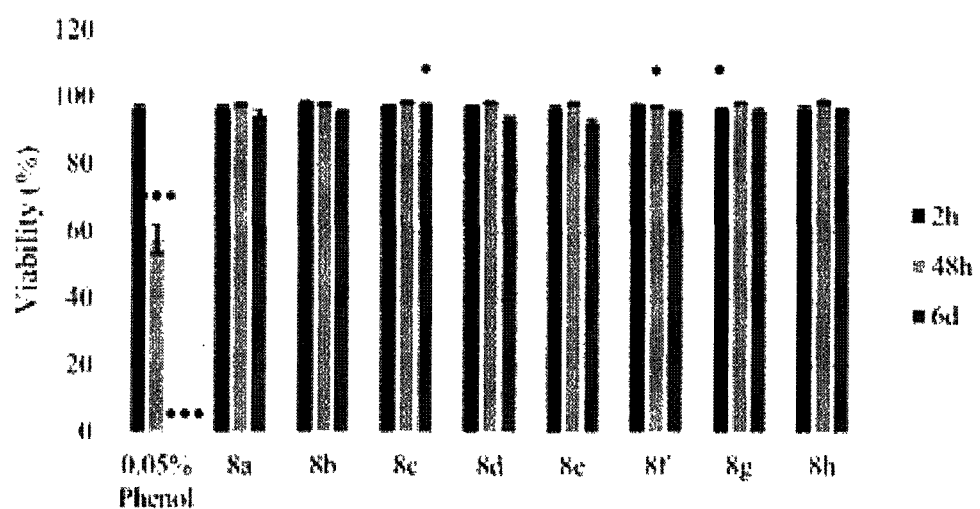
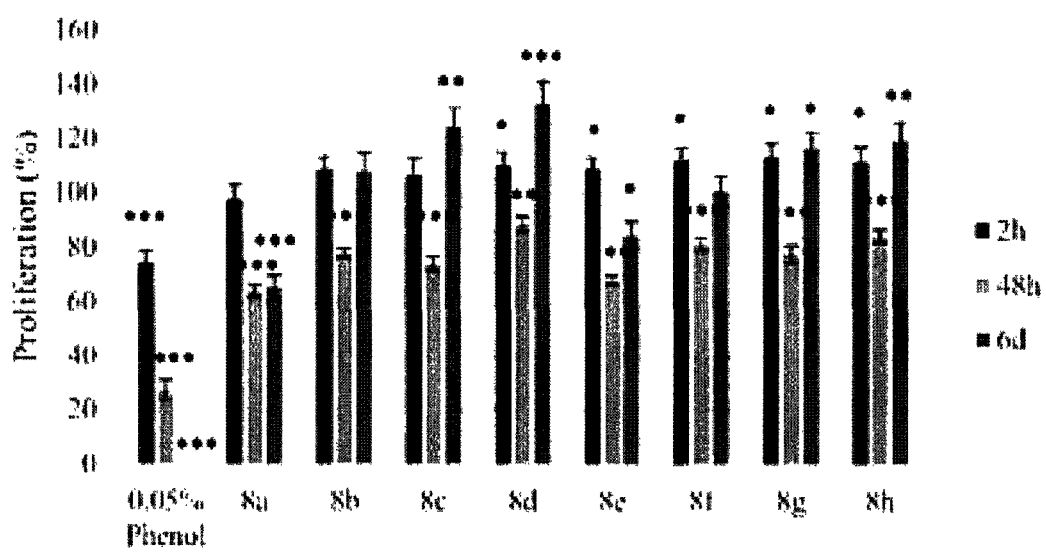

Figure 4
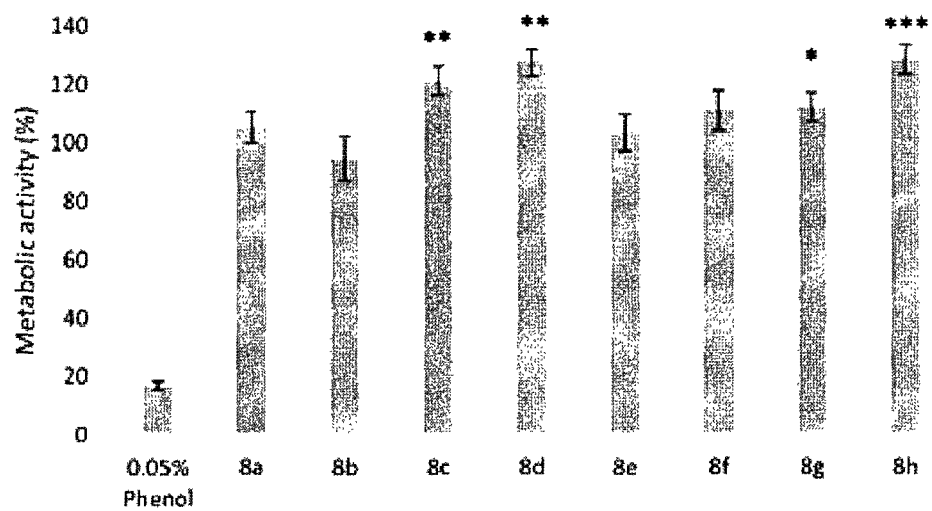
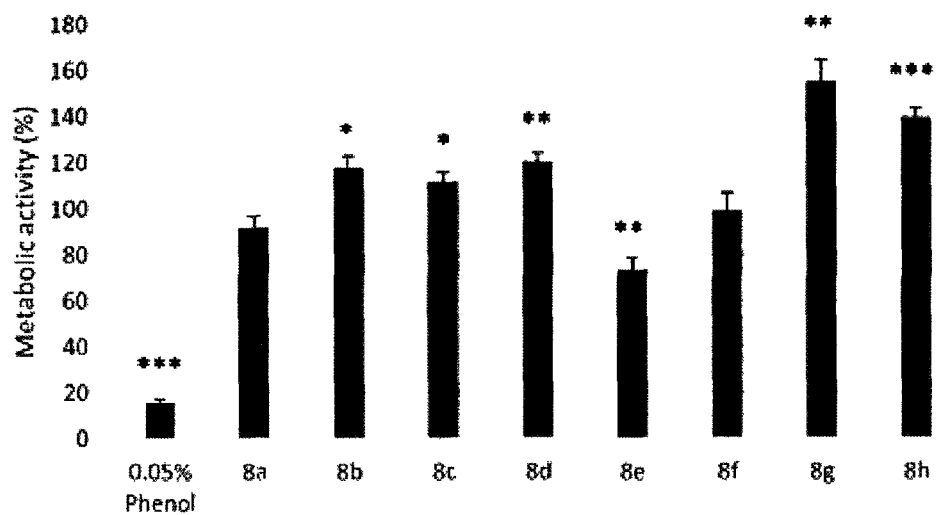

Figure 6B
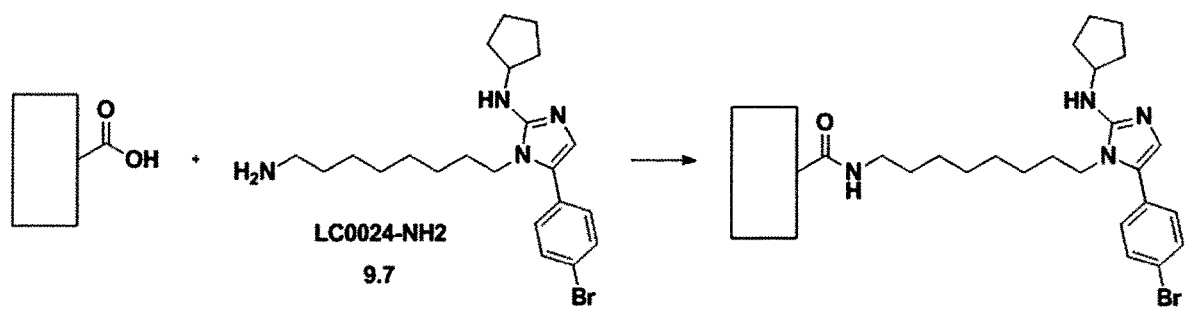
*Conditions: Oxyma, DIC, DCM, DMF, rt, 16h*
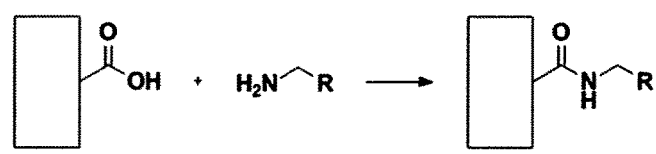
Fig. 7
A.
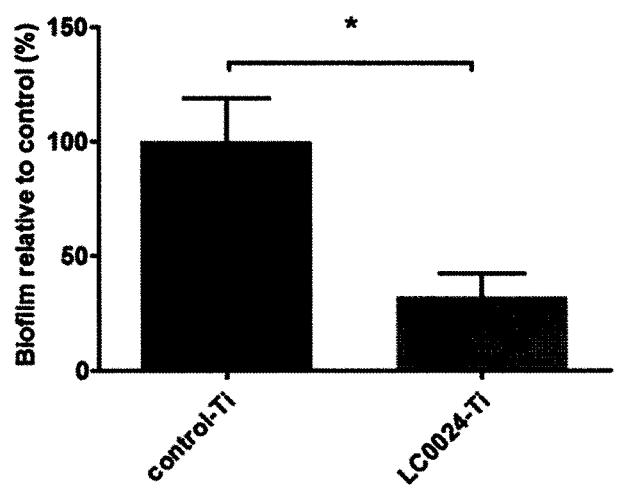

Figure 11
Non-cytotoxic control
Cytotoxic control
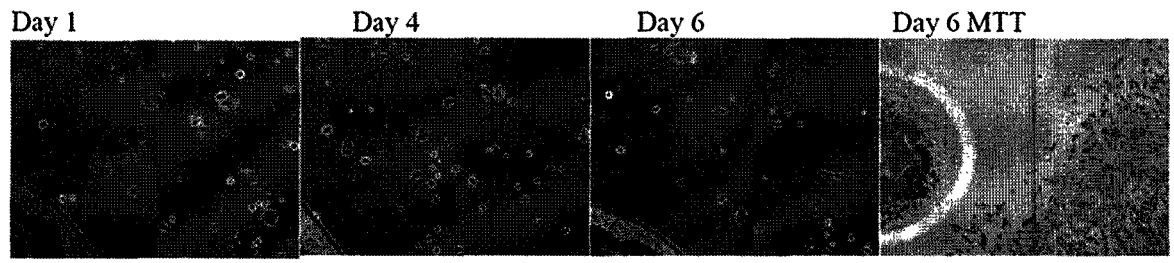
Uncoated smooth disc
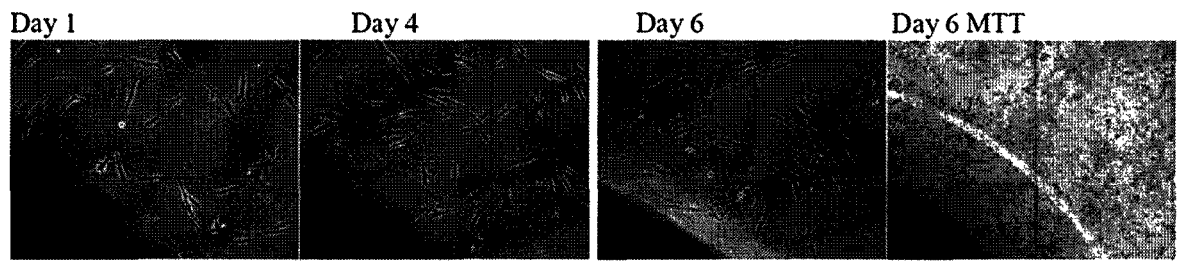
LC0024 coated smooth disc
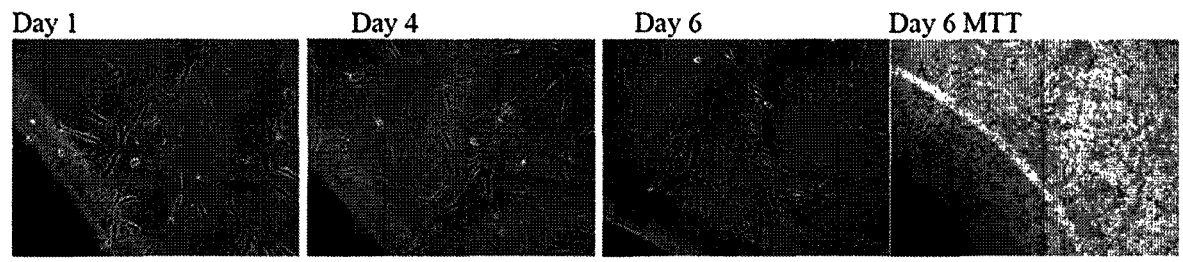

COMPOUNDS, COMPOSITIONS, AND METHODS FOR CONTROLLING BIOFILMS

FIELD OF THE INVENTION

The present invention relates to compounds, compositions and methods for controlling biofilms and microbial, in particular bacterial, growth and for reducing bacterial colonization. The present invention also relates to a surface, such as the surface of a medical device, coated with the compounds of the present invention. The present invention also relates to the treatment and prevention of infectious diseases caused by microbial biofilm formation, in particular to antimicrobial prophylactic and therapeutic compositions containing an effective amount of a biofilm formation inhibiting compound to reduce or eliminate colonization with potentially pathogenic microorganisms, more particularly bacteria (including bacterial strains resistant to many or most common antimicrobial agents), thereby reducing the risk of subsequent disease occurrence. Furthermore, the present invention relates to compounds, and to compositions and methods involving these compounds, for inhibiting, reducing or preventing the formation of a biofilm on a surface of a medical device such as a catheter, or on a tissue such as teeth, urethra or lungs of a human (e.g. a cystic fibrosis patient). These compounds, compositions and methods of the present invention are in particular useful for preventing biofilm formation in a tissue to prevent or control a chronic bacterial infection or sepsis, and also useful for sanitation when applied to a substrate with which a human or an animal may come into contact.

BACKGROUND OF THE INVENTION

Biofilms are complex, condition-dependent, surface-associated communities of microorganisms (e.g. bacterial cells) embedded in a self-produced matrix of extracellular polymeric substance. Biofilms represent a prevalent mode of microbial life in natural, industrial and hospital settings. The microbial cells growing in a biofilm are physiologically distinct from planktonic cells of the same organism. Biofilm cells exhibit profound changes in gene expression and cell physiology compared with planktonic cells, and multiple genetic pathways mediate the regulation of biofilm formation. Microorganisms in biofilms form microbial colonies or condominiums that make it easy to carry out chemical reactions that are impossible for individual microbial cells. Biofilms can contain many different types of microorganism, e.g. bacteria, archaea, protozoa, fungi and algae.

The use of effective antimicrobial compositions to avoid biofilm formation is recommended for any surface in contact with water, such as swimming pool liners, water cooling surfaces, hoses, water dispensers, water storage and distribution systems for drinking water or aquaculture, and for surfaces of medical devices such as catheters, medical implants, wound dressings and the like, especially when intended for patients with metabolic disorders.

Within biofilms bacteria are up to 1000 times more tolerant to antibiotics, disinfectants and other stress factors, which strongly impedes antimicrobial treatment. Hence persistent biofilm infections and contaminations often occur and cause a tremendous amount of problems in various sectors, including medicine, food industry, household and agriculture. In the medical sector, biofilms are often associated with implantable devices. Staphylococci are the principal microorganisms that colonize these devices. They comprise up to two-third of all pathogens in orthopedic implant infections, where they can cause septic arthritis and osteomyelitis, resulting in the inflammatory destruction of bones and joints. These infections can occur as a result of direct contamination during the operation, or as a result of microbiological spread from chronic infections elsewhere in the body. Unfortunately, the lack of a suitable treatment often leaves extraction of the contaminated device as the only viable option for eliminating the biofilm. Afterwards a prolonged antimicrobial treatment is required to make sure that the infection is eradicated.

Given the extent of problems caused by such biofilms, there has been a strong effort to develop novel anti-biofilm strategies [1-3]. One of the most promising approaches are compounds able to prevent or eradicate biofilms, without affecting the planktonic growth of the microorganisms [4, 5]. These specific anti-biofilm compounds are believed to be less prone to resistance development. Previously, we have reported the development of several series of specific anti-biofilm compounds, based on the 2-aminoimidazole (2AI) scaffold. These series include the mono-substituted 5-Aryl-2AIs (5-Ar-2AIs) (6), N1-substituted 5-Ar-2AIs (6), 2N-substituted 5-Ar-2AIs [7], 4,5-di-substituted 2AIs (6), 1,4,5-trisubstituted 2AIs (8), and 2AI-triazole-conjugates (9). These compounds were shown to display a preventive activity against biofilms of *Salmonella typhimurium*, one of the most important causes of foodborne infections worldwide and a notorious biofilm former both inside and outside the host, and of *P. aeruginosa*, a Gram-negative opportunistic pathogen that can infect immunocompromised people such as cystic fibrosis patients and cause life-threatening chronic lung infections (10). Moreover, *P. aeruginosa* biofilms can occur on a variety of medical devices such as intravascular and urinary catheters.

During the last decade, several synthetic methodologies leading to diversely substituted 2-AIs have been published [8, 9,11-13]. Our research group has developed a diversely oriented approach towards 2-AIs from 2-aminopyrimidines and α-bromoketones [12,15]. By switching reaction conditions a selective synthesis of either N1-substituted 2-AIs or 2N-substituted 2-AIs can be achieved.

In the search for new anti-biofilm compounds, most attention has been focused on monospecies biofilms, which consist of only one species. However, it has become clear that in nature, biofilms often consist of more than one microbial species. For instance, it is estimated that 27% of nosocomial *C. albicans* bloodstream infections are polymicrobial, with *S. aureus* as the third most common organism isolated in conjunction with *C. albicans*. Mixed-species biofilms are often more resilient than single-species biofilms, which has further implications for their control and manipulation in a variety of applications. Therefore, nowadays multispecies biofilms are included in much more pre-clinical research activities.

SUMMARY OF THE INVENTION

As part of the present invention it was shown that 5-Ar-2AIs substituted at both the N1- and 2N-position combine the broad-spectrum activity, in particular against Gram-positive bacteria, of the N1-substituted compounds, with the low toxicity of the 2N-substituted compounds. A series of eight novel N1-,2N-disubstituted 5-Ar-2AIs was synthesized and these compounds were shown to be non-toxic and have a broad activity against Gram-positive bacteria. So in a first aspect the present invention provides said N1-,2N-disubstituted 5-Ar-2AIs, their use in the preparation of pharmaceutical or veterinary preparations as well as methods for the elimination of biofilms involving the use of said compounds.

In a second aspect the present invention provides antibiofilm surface with low toxicity for eukaryotic cells, in particular animal or human cells, and which exhibit prolonged antibacterial and/or antibiofilm activity. Said surface coatings comprise the antibiofilm compounds of the present invention.

The present invention relates to a selected group of substituted 5-aryl-2-aminoimidazoles which exhibit a broad microbial biofilm activity, especially against a wide range of Gram-positive bacteria, and therefore can be formulated into antimicrobial compositions for administration to humans and animals and for application to inert surfaces susceptible to infection by microbial biofilms. The present invention also provides a surface, such as the surface of a medical implant, coated with the compounds of the present invention. The present invention also provides a method for suppressing, reducing, inhibiting, controlling, treating or preventing the development of a microbial biofilm on a biotic or abiotic surface or in a subject, which comprises the step of exposure or administration of such a composition on said surface or to the subject.

1. A compound selected from the group consisting of substituted 5-aryl-2-aminoimidazoles represented by the structural formula (I),

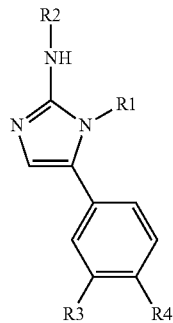

wherein,
R1 is selected from the group consisting of substituted or unsubstituted $C_{4-12}$ alkyl and $C_{3-12}$ cycloalkyl;
R2 is selected from the group consisting of substituted or unsubstituted $C_{2-3}$ alkyl, $C_{4-10}$ alkyl and $C_{3-10}$ cycloalkyl;
R3 and R4 are each independently selected from the group consisting of halogen, nitro, methoxy, methyl, hydroxyl and methylsulfonyl;
and pharmaceutically acceptable salts, hydrates, solvates, stereoisomers or polymorphic forms thereof.

2. The substituted 5-aryl-2-aminoimidazole compound according to statement 1 selected from the group consisting of N-isobutyl-1-octyl-5-phenyl-1H-imidazol-2-amine, 5-(4-chlorophenyl)-N-isobutyl-1-octyl-1H-imidazol-2-amine, 5-(4-bromophenyl)-N-isobutyl-1-octyl-1H-imidazol-2-amine, 5-(3,4-dichlorophenyl)-N-isobutyl-1-octyl-1H-imidazol-2-amine, N-cyclopentyl-1-octyl-5-phenyl-1H-imidazol-2-amine, 5-(4-chlorophenyl)-N-cyclopentyl-1-octyl-1H-imidazol-2-amine, 5-(4-bromophenyl)-N-cyclopentyl-1-octyl-1H-imidazol-2-amine, and 5-(3,4-dichlorophenyl)-N-cyclopentyl-1-octyl-1H-imidazol-2-amine.

3. A surface coated with a substituted 5-aryl-2-aminoimidazole compounds according to any one of the statements 1 or 2.

4. The surface according to statement 3, wherein said compound is coated onto a surface via an amide bond between a free amine at R1 or R2 and a carboxyl group of a linker molecule covalently bound to such surface.

5. The surface according to any one of the statements 3 or 4, wherein said surface is the surface of a veterinary or medical implant.

6. The surface according to any one of the statement 5, wherein said surface is the surface of a titanium implant.

7. A composition for use in treatment or prevention of a pathological condition associated with a microbial infection or for decreasing or eradicating bacterial growth in an animal or human, wherein said composition comprises one or more excipients and a biofilm inhibiting amount of a compound selected from the group consisting of substituted 5-aryl-2-aminoimidazoles represented by the structural formula (I),

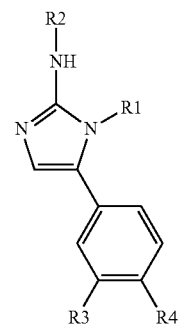

wherein,
R1 is selected from the group consisting of substituted or unsubstituted $C_{4-12}$ alkyl and $C_{3-12}$ cycloalkyl;
R2 is selected from the group consisting of substituted or unsubstituted $C_{2-3}$ alkyl, $C_{4-10}$ alkyl and $C_{3-10}$ cycloalkyl;
R3 and R4 are each independently selected from the group consisting of halogen, nitro, methoxy, methyl, hydroxyl and methylsulfonyl;
and pharmaceutically acceptable salts, hydrates, solvates, stereoisomers or polymorphic forms thereof.

8. The composition according to statement 7, wherein said composition comprises a compound selected from the group consisting of N-isobutyl-1-octyl-5-phenyl-1H-imidazol-2-amine, 5-(4-chlorophenyl)-N-isobutyl-1-octyl-1H-imidazol-2-amine, 5-(4-bromophenyl)-N-isobutyl-1-octyl-1H-imidazol-2-amine, 5-(3,4-dichlorophenyl)-N-isobutyl-1-octyl-1H-imidazol-2-amine, N-cyclopentyl-1-octyl-5-phenyl-1H-imidazol-2-amine, 5-(4-chlorophenyl)-N-cyclopentyl-1-octyl-1H-imidazol-2-amine, 5-(4-bromophenyl)-N-cyclopentyl-1-octyl-1H-imidazol-2-amine, and 5-(3,4-dichlorophenyl)-N-cyclopentyl-1-octyl-1H-imidazol-2-amine.

9. A method for treating a microbial infection or for inhibiting microbial biofilm formation in a plant, or on a surface with which a human or an animal may come into contact, by applying to said plant or surface, an antimicrobial composition according to any one of the statements 7 or 8.

10. The use of a composition for disinfecting or sterilizing a surface ex vivo to decrease or eradicate a biofilm or prevent biofilm growth, wherein said composition comprises a biofilm inhibiting amount of a compound selected from the group consisting of substituted 5-aryl-2-aminoimidazoles represented by the structural formula (I)

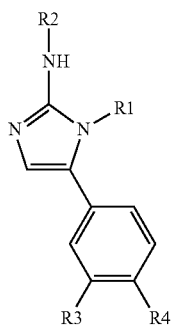

wherein,
R1 is selected from the group consisting of substituted or unsubstituted $C_{4-12}$ alkyl and $C_{3-12}$ cycloalkyl;
R2 is selected from the group consisting of substituted or unsubstituted $C_{2-3}$ alkyl, $C_{4-10}$ alkyl and $C_{3-10}$ cycloalkyl;
R3 and R4 are each independently selected from the group consisting of halogen, nitro, methoxy, methyl, hydroxyl and methylsulfonyl;
and pharmaceutically acceptable salts, hydrates, solvates, stereoisomers or polymorphic forms thereof.

11. The use of a composition according to statement 10, wherein said composition comprises a compound selected from the group consisting of N-isobutyl-1-octyl-5-phenyl-1H-imidazol-2-amine, 5-(4-chlorophenyl)-N-isobutyl-1-octyl-1H-imidazol-2-amine, 5-(4-bromophenyl)-N-isobutyl-1-octyl-1H-imidazol-2-amine, 5-(3,4-dichlorophenyl)-N-isobutyl-1-octyl-1H-imidazol-2-amine, N-cyclopentyl-1-octyl-5-phenyl-1H-imidazol-2-amine, 5-(4-chlorophenyl)-N-cyclopentyl-1-octyl-1H-imidazol-2-amine, 5-(4-bromophenyl)-N-cyclopentyl-1-octyl-1H-imidazol-2-amine, and 5-(3,4-dichlorophenyl)-N-cyclopentyl-1-octyl-1H-imidazol-2-amine.

12. The use of a composition according to any one of the statements 10 or 11, wherein said composition comprises one or more excipients.

13. The use of a composition according to any one of the statements 10 to 12, wherein said excipient is a solvent for said compound.

14. The use of a composition according to claim 13, wherein said solvent is selected from the group consisting of dimethylformamide, tetrahydrofuran, acetonitrile, dichloromethane, N-methylpyrrolidone, acetone, chloroform, dimethylsulfoxide and mixtures thereof.

BRIEF DESCRIPTION OF THE DRAWINGS

FIG. 2 Synthesis and structures of eight novel N1-,2N-disubstituted 5-Ar-2AIs.
FIG. 3 Effect of selected compounds (12.5 µM) on the proliferation and viability of osteoblasts (OB, FIG. 3B) and mesenchymal stem cells (MSC, FIG. 3A) after 2 h, 48 h and 6 days of exposure, as determined by trypan blue staining. Bars and error bars represent resp. means and standard errors of 8 repeats. Negative control was cell culture medium with 0.5% ethanol solvent background, positive control was 0.05% phenol to show a cytotoxic effect. % proliferation is defined as: (total viable cells in treated sample/total viable cells in solvent control)×100. % viability is defined as: (total viable cells (unstained)/total cells (stained+unstained))×100. Significant differences ($p<0.05=*$; $p<0.01=$ and $p<0.001=*$) with the negative control are indicated.

FIG. 4 Effect of selected compounds (12.5 µM) on the metabolic activity of osteoblasts (OB) and mesenchymal stem cells (MSC) after 6 days of exposure, as determined by MTT staining. Bars and error bars represent resp. means and standard errors of 4 repeats. Negative control was cell culture medium with 0.5% ethanol solvent background, positive control was 0.05% phenol to show a cytotoxic effect. Significant differences ($p<0.05=*$; $p<0.01=$ and $p<0.001=*$) with the negative control are indicated.

FIG. 7 In vitro characterization of biofilm formation of S. aureus on LC0024-Ti discs (LC0024 is compound 8g from FIG. 2). The percentage of S. aureus SH1000 biofilm cells present on the surface of the coated titanium discs (LC0024-Ti discs) as compared to the control discs (control-Ti discs) to which no compound was coupled. Data represent the mean±standard errors of the means (SEM) of three independent experiments ($P<0.05=*$).

FIG. 11 Human bone marrow derived stromal cell morphology after the direct contact cytotoxicity test.

DEFINITIONS

Figure 1:
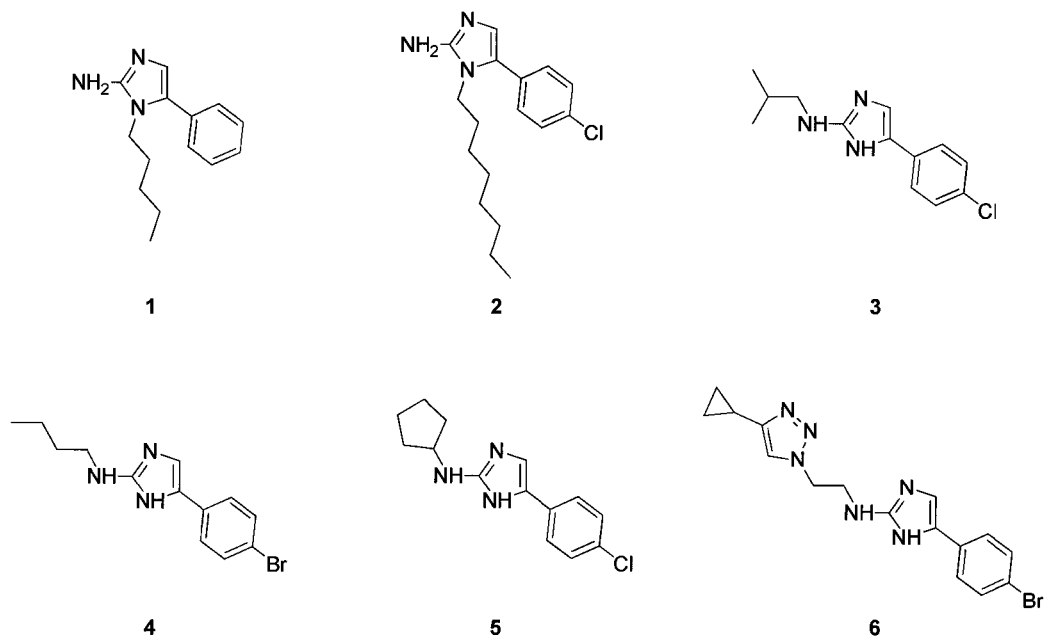
FIG. 1 Structures of 5-Ar-2AI based compounds.

Reference throughout this specification to "one embodiment" or "an embodiment" means that a particular feature, structure or characteristic described in connection with the embodiment is included in at least one embodiment of the present invention. Thus, appearances, of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from the present invention, in one or more embodiments. Where an indefinite or definite article is used when referring to a singular noun e.g. "a" or "an", "the", this includes a plural of that noun unless something else is specifically stated.

Similarly, it should be appreciated that in the description of exemplary embodiments of the invention, various features of the invention are sometimes grouped together in a single embodiment, figure, or description thereof for the purpose of streamlining the present invention and aiding in the understanding of one or more of the various inventive aspects.

As used herein the terms "reducing", "suppressing", "inhibiting", "decreasing", "removing" or the like in reference to microorganisms or a biofilm or biofilm formation means complete or partial inhibition (more than 50%, preferably more than 90%, still more preferably more than 95% or even more than 99%) of microorganisms or biofilm formation (in the term of number of remaining cells or remaining total biomass) and/or development and also includes within its scope the reversal of microorganisms or biofilm development or processes associated with microorganisms or biofilm formation and/or development. Further, inhibition may be permanent or temporary. In terms of temporary inhibition, microorganisms or biofilm formation and/or development may be inhibited for a time sufficient to produce the desired effect (for instance at least 5 days, preferably at least 10 days). Preferably, the inhibition of microorganisms or a biofilm is complete and/or permanent (no persisters) ("eradicating").

As used herein, "preventing" or the like in reference to microorganisms or a biofilm or biofilm formation means complete or partial prevention (more than 50%, preferably more than 90%, still more preferably more than 95% or even more than 99%) of microorganisms or biofilm formation (in the term of number of remaining cells or remaining total biomass) and also includes within its scope processes associated with microorganisms or biofilm formation. Further, prevention may be permanent or temporary. In terms of temporary prevention, microorganisms or biofilm formation may be inhibited for a time sufficient to produce the desired effect (for instance at least 5 days, preferably at least 10 days). Preferably, the prevention of microorganisms or biofilm is complete and/or permanent.

As used herein the term "exposing" means administering to, or otherwise bringing into contact with. A microorganism or biofilm may be exposed to an active agent directly or indirectly. Typically direct exposure refers to administration of the agent to the microorganism or biofilm to be treated or otherwise bringing the microorganism or biofilm into contact with the agent itself. Typically indirect exposure refers to the administration of a precursor of the active agent or a compound or molecule capable of generating, either solely or in reaction with other compounds or molecules, the active agent to the microorganism or biofilm or otherwise bringing the microorganism or biofilm into contact therewith. Similarly, the terms "treat" and "treating" and variations thereof as used herein mean administering to, or otherwise bringing into contact with.

The term "optionally substituted" indicates that the specified group is either unsubstituted, or substituted by one or more suitable substituents. A "substituent" as defined herein is a monovalent atom or group of atoms replacing a hydrogen atom on a hydrocarbon chain or cycle (ring) of an organic molecule, for example halogen, hydroxy, acyl, alkyl, alkenyl, alkynyl, cycloaliphatic, heterocyclo, aryl (in particular phenyl), heteroaryl, alkoxy (such as methoxy), amino, amido, sulfhydryl, alkylthio, alkylsulfonyl (such as methylsulfonyl), nitro, carbonyl, carboxy, amino-acid (both natural and synthetic) and peptido, or a divalent atom replacing two hydrogen atoms on the same carbon atom of a hydrocarbon chain, for instance oxo or thioxo. The number of admissible substituents depends upon the number of hydrogen atoms that can be replaced, thus the chain length, the type of substituent and parameters such as steric hindrance which are well known to the skilled person.

The term "aliphatic" as used herein refers to "Alkyl", "Alkenyl" or "Alkynyl". The term "alkyl" or "saturated aliphatic" as used herein, and unless otherwise specified, refers to a straight or branched hydrocarbon chain containing from 1 to 20 (e.g. 2, 3, 4, 5, 6, 7, 8, 9, 10, 11, 12, 13, 14, 15, etc.) carbon atoms, hence the notation $C_{1-20}$ alkyl, preferably containing from 4 to 12 (e.g. 4, 5, 6, 7, 8, 9, 10, 11 or 12) carbon atoms, hence the notation $C_{4-12}$ alkyl, or containing from 2 to 3 carbon atoms, hence the notation $C_{2-3}$ alkyl or from 4 to 10 (e.g. 2, 3, 4, 5, 6, 7, 8, 9 or 10) carbon atoms, hence the notation $C_{4-10}$ alkyl. Representative examples of $C_{1-20}$ alkyl, $C_{4-12}$ alkyl, $C_{2-3}$ alkyl, or $C_{4-10}$ alkyl, include, but are not limited to, methyl, ethyl, n-propyl, isopropyl, n-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. Such alkyl groups may optionally be substituted with one or more (e.g. 2, 3 or 4) substituents as defined hereinabove.

"Alkenyl," as used herein, refers to a straight or branched hydrocarbon chain containing from 2 to 20 carbon atoms, hence the notation $C_{2-20}$ alkenyl, and containing at least one carbon-carbon double bond. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, butadienyl, hexadienyl and the like. Such alkenyl groups may optionally be substituted with one or more (e.g. 2, 3 or 4) substituents as defined hereinabove.

"Alkynyl" as used herein, refers to a straight or branched hydrocarbon chain containing from 2 to 20 carbon atoms, hence the notation $C_{2-20}$ alkynyl, and containing at least one carbon-carbon triple bond. Representative examples of $C_{2-20}$ alkynyl include, but are not limited, to acetylenyl, 1-propynyl, 2-propynyl, 3-butynyl, 2-pentynyl, 1-butynyl and the like. Such alkynyl groups may optionally be substituted with one or more (e.g. 2, 3 or 4) substituents as defined hereinabove.

The term "cycloaliphatic", as used herein and unless otherwise specified, refers to a saturated or ethylenically unsaturated monocyclic or polycyclic hydrocarbon group containing from 3 to 10 (e.g. 3, 4, 5, 6, 7, 8, 9 or 10) or from 3 to 12 (e.g. 3, 4, 5, 6, 7, 8, 9, 10, 11 or 12) carbon atoms, which is not aromatic, hence the notations $C_{3-10}$ cycloalkyl or $C_{3-12}$ cycloalkyl (saturated) and $C_{3-22}$ cycloalkenyl (unsaturated). Representative examples of cycloalkyl include, but are not limited to, cyclopropyl, cyclobutyl, cyclopentyl, cyclohexyl, cycloheptyl, tricyclodecyl, cyclododecyl, adamantyl, nornornyl, 5,6-trimethylenenorborn-2-yl and cyclooctyl. Such cycloaliphatic groups may optionally be substituted with one or more (e.g. 2, 3 or 4) substituents as defined hereinabove. Representative examples of cycloalkenyl include, but are not limited to, cyclopropenyl, cyclobutenyl, cyclopentenyl, cyclohexenyl, cycloheptenyl, cyclooctenyl, cyclononenyl, cyclodecenyl, 1,3-cyclohexadienyl, 1,4-cyclohexadienyl, 1,3-cycloheptadienyl, 1,5-cyclooctadienyl.

The term "heterocyclic", as used herein, refers to a saturated or ethylenically unsaturated but not aromatic monocyclic or polycyclic (e.g. bicyclic) ring system comprising at least one heteroatom preferably selected from the group consisting of nitrogen, oxygen and sulfur in at least one ring. Monocyclic heterocyclic ring systems are exemplified by any 3 to 8 (e.g. 4, 5 or 6 or 7) member ring containing 1, 2, 3, or 4 heteroatoms independently selected from the group consisting of O, N, and S. A 5 member ring has from 0 to 2 double bonds, and a 6 member ring has from 0-3 double bonds. Depending upon the number of double bonds, the heterocyclic ring system may be heteroaromatic (see specific definition below) or not. Representative examples of monocyclic non-aromatic heterocyclic ring systems include, but are not limited to, azetidine, azepine, aziridine, diazepine, 1,3-dioxolane, 1,2-dioxane, 1,3-dioxane, 1,4-dioxane, 1,2-dithiane, 1,3-dithiane, 1,4-dithiane, imidazoline, imidazolidine, isothiazoline, isothiazolidine, isoxazoline, isoxazolidine, morpholine, oxadiazoline, oxadiazolidine, oxazoline, oxazolidine, piperazine, piperidine, pyrazine, pyrazoline, pyrazolidine, pyrroline, pyrrolidine, tetrahydrofuran, tetrahydrothiophene, thiadiazoline, thiadiazolidine, thiazoline, thiazolidine, thiomorpholine, thiomorpholine sulfone, thiomorpholine sulfoxide, and the like. Bicyclic ring systems are exemplified by any of the above monocyclic ring systems fused to an aryl or cycloalkyl or heterocyclic group as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like.

"Aromatic" as used herein refers to a ring system having one or more aromatic rings, which may be homoaromatic or heteroaromatic.

"Homoaromatic" or "aryl" as used herein refers to an aromatic ring system in which no carbon atoms have been replaced with heteroatoms. The homoaromatic group can be unsubstituted or substituted with from 1 to 5 suitable substituents as defined hereinabove, and wherein two adjacent substituents may be linked to form a cycle such as methylenedioxy. Representative examples of aryl include, but are not limited to, azulenyl, indanyl, indenyl, naphthyl, phenyl, tetrahydronaphthyl, and mono- and polysubstituted versions thereof.

"Heteroaromatic" or "heteroaryl" as used herein refers to an aromatic ring system in which one or more carbon atoms have been replaced with heteroatoms independently selected from the group consisting of nitrogen, oxygen and sulfur in at least one ring. Examples of heteroaryl include, but are not limited to, pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, isoxazolyl, oxazolyl, dioxazolyl, pyrazolyl, tetrazinyl, tetrazolyl, thiadiazolyl, thiazolyl, triazinyl and benzo[b]thienyl. The heteroaryl group may be optionally substituted with one or more, e.g. 1 to 4, suitable substituents as defined hereinabove.

The term "alkoxy" as used herein refers to substituents wherein a carbon atom of a alkyl group (such as defined herein), is attached to an oxygen atom through a single bond such as, but not limited to, methoxy, ethoxy, propoxy, isopropoxy, butoxy, iso-butoxy, sec-butoxy, tert-butoxy, pentoxy, 3-pentoxy, or n-hexyloxy.

The term "alkylthio" as used herein refers to substituents wherein a carbon atom of a alkyl group (such as defined herein), is attached to an sulfur atom through a single bond such as, but not limited to, methylthio, ethylthio, etc.

As used herein and unless otherwise stated, the term halogen means any atom selected from the group consisting of fluorine, chlorine, bromine and iodine.

The term "microorganism", as used herein, refers to unicellular or cell-cluster microscopic organisms including eukaryotes such as fungi and protists, and prokaryotes, especially microorganisms that are susceptible to cause a disease in humans, but excluding a virus or a prion. These microorganisms can be organized in the form of a biofilm, thus the term "microbial biofilm".

As used herein the term "biofilm" refers to a mode of microbial growth comprising sessile cells, usually within a complex and highly heterogeneous matrix of extracellular polymers, and characterized by a reduced sensitivity to antimicrobial agents. In the context of the present invention, "biofilms" can contain single species such as bacteria including but not limited to *S. thypimurium, S. epidermis, P. aeruginosa, E. coli, S. aureus, S. liquefaciens, B. cepacia, P. gingivalis*, or a fungi/yeast including but not limited to *C. albicans*. In the context of the present invention, "biofilms" can also contain multiple species microorganisms such as yeasts including but not limited to *C. albicans*, and/or other microorganisms such as bacteria including but not limited to *E. coli, S. epidermis, S. aureus, P. aeruginosa*.

The term "antimicrobial" as used herein means that the composition of the present invention reduces, eradicates, inhibits or prevents the growth or proliferation of, a microbe or microorganism. The term "antimicrobial" may hence refer to antibacterial, antibiofilm, antiviral, antiprotozoan and/or antifungal activity.

The term "sepsis", as used herein, refers to a systemic inflammatory response syndrome associated to an infection. Septic shock is characterized namely by (a) hypotension persisting despite adequate fluid resuscitation, and (b) abnormalities related to hypoperfusion or organ dysfunction.

DETAILED DESCRIPTION OF THE INVENTION

As compared to our previous studies on substituted 2-aminoimidazoles (WO2011080132), the present invention provides a selection of novel compounds wherein said compounds show a surprisingly better activity against Gram-positive bacteria.

In a first object the present invention presents a substituted 5-aryl-2-aminoimidazole compound represented by the structural formula (I) wherein R1 is selected from the group comprising substituted or unsubstituted $C_{4-12}$ alkyl and $C_{3-12}$ cycloalkyl; R2 is selected from the group comprising substituted or unsubstituted $C_{2-3}$ alkyl, $C_{4-12}$ alkyl and $C_{3-12}$ cycloalkyl; and R3 and R4 are each independently selected from the group comprising halogen, nitro, $C_{1-12}$ alkoxy, $C_{1-12}$ alkyl, hydroxyl and methylsulfonyl.

In a preferred embodiment of the present invention, said substituted 5-aryl-2-aminoimidazole compound is represented by the structural formula (I) wherein R1 is selected from the group consisting of substituted or unsubstituted $C_{4-12}$ alkyl and $C_{3-12}$ cycloalkyl; R2 is selected from the group consisting of substituted or unsubstituted $C_{2-3}$ alkyl, $C_{4-10}$ alkyl and $C_{3-10}$ cycloalkyl; and R3 and R4 are each independently selected from the group consisting of halogen, nitro, methoxy, methyl, hydroxyl and methylsulfonyl.

Typically, the compounds of the present invention also include pharmaceutically acceptable salts, hydrates, solvates, stereoisomers or polymorphic forms thereof.

In a preferred embodiment of the present invention, said compound is selected from the group comprising N-isobutyl-1-octyl-5-phenyl-1H-imidazol-2-amine, 5-(4-chlorophenyl)-N-isobutyl-1-octyl-1H-imidazol-2-amine, 5-(4-bromophenyl)-N-isobutyl-1-octyl-1H-imidazol-2-amine, 5-(3,4-dichlorophenyl)-N-isobutyl-1-octyl-1H-imidazol-2-amine, N-cyclopentyl-1-octyl-5-phenyl-1H-imidazol-2-amine, 5-(4-chlorophenyl)-N-cyclopentyl-1-octyl-1H-imidazol-2-amine, 5-(4-bromophenyl)-N-cyclopentyl-1-octyl-1H-imidazol-2-amine, and 5-(3,4-dichlorophenyl)-N-cyclopentyl-1-octyl-1H-imidazol-2-amine.

Typically, the compounds of the present invention as described herein are used in the treatment or prevention of a microbial biofilm associated condition or infection in a human or animal subject. Preferably, said microbial biofilm associated condition or infection is a bacterial, fungal or yeast biofilm associated condition or infection. Said microbial biofilm may also comprise a combination of bacterial and/or fungal and/or yeast microorganisms.

In a second object the present invention presents a surface coated with any of the compounds according to the first object of the present invention.

In a preferred embodiment of the present invention, said compound is coated onto a surface via an amide bond between a free amine at R1 or R2 and a carboxyl group of a linker molecule covalently bound to such surface.

Preferably, said surface is the surface of a veterinary or medical implant. More preferably, said implant is a titanium implant.

Interestingly, it was shown that implants coated with the compounds according the present invention had favorable osseointegration characteristics. Therefore, the compounds according to the present invention are particularly suited for the coating of surfaces of implants destined to integrate in bone tissue.

Preferably, said surfaces are coated with said compounds at a concentration of 0.01 nmol/cm² to 10 nmol/cm², more preferably at a concentration of 0.1 nmol/cm² to 1 nmol/cm², even more preferably at a concentration of 0.1 nmol/cm² to 0.5 nmol/cm².

In a third object the present invention presents a composition for use in treatment or prevention of a pathological condition associated with a microbial infection or for decreasing or eradicating bacterial growth in an animal or human, wherein said composition comprises one or more excipients and a biofilm inhibiting amount of a compound selected from the group consisting of substituted 5-aryl-2-aminoimidazoles represented by the structural formula (I), wherein, R1 is selected from the group comprising substituted or unsubstituted $C_{4-12}$ alkyl and $C_{3-12}$ cycloalkyl; R2 is selected from the group comprising substituted or unsubstituted $C_{2-3}$ alkyl, $C_{4-12}$ alkyl and $C_{3-12}$ cycloalkyl; and R3 and R4 are each independently selected from the group comprising halogen, nitro, $C_{1-12}$alkoxy, $C_{1-12}$ alkyl, hydroxyl and methylsulfonyl.

In a preferred embodiment of the present invention, said composition comprises one or more excipients and a biofilm inhibiting amount of a compound selected from the group consisting of substituted 5-aryl-2-aminoimidazoles represented by the structural formula (I), wherein, R1 is selected from the group consisting of substituted or unsubstituted $C_{4-12}$ alkyl and $C_{3-12}$ cycloalkyl; R2 is selected from the group consisting of substituted or unsubstituted $C_{2-3}$ alkyl, $C_{4-10}$ alkyl and $C_{3-10}$ cycloalkyl; and R3 and R4 are each independently selected from the group consisting of halogen, nitro, methoxy, methyl, hydroxyl and methylsulfonyl.

Typically, the compositions of the present invention also include pharmaceutically acceptable salts, hydrates, solvates, stereoisomers or polymorphic forms thereof.

In a preferred embodiment, said composition comprises a compound selected from the group comprising N-isobutyl-1-octyl-5-phenyl-1H-imidazol-2-amine, 5-(4-chlorophenyl)-N-isobutyl-1-octyl-1H-imidazol-2-amine, 5-(4-bromophenyl)-N-isobutyl-1-octyl-1H-imidazol-2-amine, 5-(3,4-dichlorophenyl)-N-isobutyl-1-octyl-1H-imidazol-2-amine, N-cyclopentyl-1-octyl-5-phenyl-1H-imidazol-2-amine, 5-(4-chlorophenyl)-N-cyclopentyl-1-octyl-1H-imidazol-2-amine, 5-(4-bromophenyl)-N-cyclopentyl-1-octyl-1H-imidazol-2-amine, and 5-(3,4-dichlorophenyl)-N-cyclopentyl-1-octyl-1H-imidazol-2-amine.

Typically, said compositions of the present invention as described herein are used in the treatment or prevention of a microbial biofilm associated condition or infection in a human or animal subject. Preferably, said microbial biofilm associated condition or infection is a bacterial, fungal or yeast biofilm associated condition or infection. Said microbial biofilm may also comprise a combination of bacterial and/or fungal and/or yeast microorganisms.

Typically, the said compositions of the present invention as described herein may, either for improved efficiency or for controlling several types of microbes in the same or a vicinal locus of a human, an animal or a plant, further comprise an effective amount of another anti-microbial (e.g. antibacterial, antiprotozoal or antifungal) entity or agent. Such combination of active agents may be in the form of a kit wherein each agent is kept separate until effective use. The other anti-microbial entity may be a biocide, an antibiotic agent or another specific therapeutic entity. Suitable antibiotic agents include, without limitation, penicillin, quinoline, vancomycin, sulfonamides, ampicillin, ciprofloxacin, and sulfisoxazole. The specific therapeutic entity can include a targeting moiety coupled to an anti-microbial peptide moiety.

Typically, said compositions of the present invention as described herein may, depending upon the desired mode of administration or application, be formulated in very different forms such as, but not limited to, liquids, gels, foams, semi-solids and solids. Practically these compositions can be in the form of an oral tablet, a capsule, a nasal aerosol, a liquid, such as throat wash, mouth wash or gargle, a toothpaste or a topical ointment. They can be in the form of tampons, rinses, creams or aerosols, soaps, hair shampoos, antiperspirants, facial tissues, skin cleansers, component of a wound dressing or any device suitable for sanitation or hygienic treatment.

When the antimicrobial compositions of this invention are formulated as liquids, at least one excipient may be a solvent for the biologically effective substituted 5-aryl-2-aminoimidazole. Said solvent may be dimethylformamide, tetrahydrofuran, acetonitrile, dichloromethane, N-methylpyrrolidone, acetone, chloroform, dimethylsulfoxide and mixtures thereof, but is not limited thereto. The respective proportions of the active compound and the solvent in the liquid formulation are mainly determined by the solubility limit of the active compound in the relevant solvent, which can readily be determined by the skilled person. A liquid antimicrobial composition of this invention may also be in the form of a kit where the active compound and the solvent are kept separately until effective use.

For an effective treatment, since the substituted 5-aryl-2-aminoimidazole may become toxic above a certain concentration, it is necessary for safety reasons to provide administration or application in the form of a composition comprising one or more excipients. Particularly preferred are compositions comprising an excipient which is agriculturally acceptable for application to a plant, or an excipient which is pharmaceutically or veterinarily acceptable for administration to, or contact with, a human or an animal.

The compositions of the present invention can include one or more non-active excipients or ingredients, e.g., ingredients that do not interfere with the biofilm inhibiting function of the active compound. The non-active ingredient can be a powder, an encapsulated solid, or an aqueous carrier. In one embodiment, the compositions of the present invention in oral form may include, without limitation, thickening materials, humectants, water, buffering agents, surfactants, titanium dioxide, flavouring systems, sweetening agents, colouring agents, and mixtures thereof. Pharmaceutically acceptable excipients, ingredients and carriers are well known, and one skilled in the pharmaceutical art can easily select them for any particular route of administration (Remington's Pharmaceutical Sciences, Mack Publishing Co., Easton, Pa., 1985).

Preferably the antimicrobial compositions of this invention are formulated for long-term storage such as concentrated solutions or lyophilized powder preparations. They may also be included in vesicles, e.g. liposomes, or be formulated as controlled release systems, using controlled release technologies known in the art.

When the antimicrobial compositions of this invention are formulated as gels or foams, they may be enclosed within a dispensing device for gel or foam.

In a fourth object the present invention presents a method for treating a microbial infection or for inhibiting microbial biofilm formation in a plant, or on a surface with which a human or an animal may come into contact, by applying to said plant or surface, an antimicrobial compound or composition according to any one of previous objects of the present invention.

When intended for a human or an animal such as, but not limited to, a mammal, a domestic animal or cattle, the method of treatment of this invention may be by administering the anti-microbial composition intravesicularly, topically, orally, rectally, ocularly, otically, nasally, parenterally, vaginally, intravenously, topically to an infected body part of said human or animal. Said body part may be an epithelial surface or a mucosal surface. Said mucosal surface may be a buccal cavity, vagina, gastrointestinal tract or oesophageal tract. When intended for disinfecting a surface which may come into contact with a human or an animal such as, but not limited to, a medical device or an implantable device (e.g. a prosthetic device, a heart valve, a pacemaker, a dental device, a stent or a catheter or a prosthetic bladder material), the method of treatment of this invention may be by dipping said medical device into the anti-microbial composition. The surface to be disinfected may be e.g. a biological surface or an inert solid industrial or domestic surface such as a heat exchanger, an air-filtering device, a component of an aquaculture system, kitchenware or a pipeline, or a surface in a hospital such as in a surgery unit where sanitization is essential. The material from which said surface is made is not a critical parameter of the method of the invention, as soon as it is susceptible to biofilm formation. The surface can include a plastic such as a silicone or another type of polymeric material.

In a fifth object the present invention presents the use of a composition for disinfecting or sterilizing a surface ex vivo to decrease or eradicate a biofilm or prevent biofilm growth, wherein said composition comprises a biofilm inhibiting amount of a compound selected from the group consisting of substituted 5-aryl-2-aminoimidazoles represented by the structural formula (I) wherein, R1 is selected from the group comprising substituted or unsubstituted $C_{4-12}$ alkyl and $C_{3-12}$ cycloalkyl; R2 is selected from the group comprising substituted or unsubstituted $C_{2-3}$ alkyl, $C_{4-12}$ alkyl and $C_{3-12}$ cycloalkyl; and R3 and R4 are each independently selected from the group comprising halogen, nitro, $C_{1-12}$ alkoxy, $C_{1-12}$ alkyl, hydroxyl and methylsulfonyl.

In a preferred embodiment of the present invention, said composition comprises a biofilm inhibiting amount of compound selected from the group consisting of substituted 5-aryl-2-aminoimidazoles represented by the structural formula (I), wherein, R1 is selected from the group consisting of substituted or unsubstituted $C_{4-12}$ alkyl and $C_{3-12}$ cycloalkyl; R2 is selected from the group consisting of substituted or unsubstituted $C_{2-3}$ alkyl, $C_{4-10}$ alkyl and $C_{3-10}$ cycloalkyl; and R3 and R4 are each independently selected from the group consisting of halogen, nitro, methoxy, methyl, hydroxyl and methylsulfonyl.

Typically, the compositions of the present invention also include pharmaceutically acceptable salts, hydrates, solvates, stereoisomers or polymorphic forms thereof.

In a preferred embodiment, said composition comprises a compound selected from the group comprising N-isobutyl-1-octyl-5-phenyl-1H-imidazol-2-amine, 5-(4-chlorophenyl)-N-isobutyl-1-octyl-1H-imidazol-2-amine, 5-(4-bromophenyl)-N-isobutyl-1-octyl-1H-imidazol-2-amine, 5-(3,4-dichlorophenyl)-N-isobutyl-1-octyl-1H-imidazol-2-amine, N-cyclopentyl-1-octyl-5-phenyl-1H-imidazol-2-amine, 5-(4-chlorophenyl)-N-cyclopentyl-1-octyl-1H-imidazol-2-amine, 5-(4-bromophenyl)-N-cyclopentyl-1-octyl-1H-imidazol-2-amine, and 5-(3,4-dichlorophenyl)-N-cyclopentyl-1-octyl-1H-imidazol-2-amine.

In another preferred embodiment, said composition comprises one or more excipients. In another preferred embodiment, said excipient is a solvent for said compound. In an even more preferred embodiment, said solvent is selected from the group comprising dimethylformamide, tetrahydrofuran, acetonitrile, dichloromethane, N-methylpyrrolidone, acetone, chloroform, dimethylsulfoxide and Typically, the compositions of the present invention as described herein may be co-administered or co-applied with one or more other antibacterial agents.

The compositions and methods of this invention are especially useful for treating or preventing a pathologic condition associated with a microbial infection or for decreasing bacterial growth in an animal or a human in need of such treatment.

The compositions and methods of this invention are especially useful for treating a human with a wound selected from the group consisting of an ulcer, a laceration, a deep penetrating wound and a surgical wound.

The compositions and methods of this invention are also useful for reducing the risk of bacterial infection or sepsis in a person colonized with pathogenic bacteria. This is especially relevant to immuno-compromised patients affected with leukaemia, lymphoma, carcinoma, sarcoma, allogenic transplant, congenital or acquired immunodeficiency, cystic fibrosis, and AIDS.

The compositions and methods of this invention are especially useful for reducing or eradicating the risk of bacterial infection in a human, wherein the pathogenic bacteria are gram positive bacteria selected from the group consisting of pneumococcal species, methicillin-resistant *Staphylococcus aureus, S. epidermidis, S. hominis, S. haemolyticus, S. capitis, S. warneri*, multi-drug resistant, *Streptococcus* spp., *Enterococcus* spp., *Propionibacterium acnes*.

The compositions and methods of this invention are also useful for reducing or eradicating the risk of bacterial infection in a person, wherein the pathogenic bacteria are gram negative bacteria selected from the group consisting of *Salmonella*, e.g. *S. typhimurium, S. enteritidis, S. arizonae, S. bongori, S. choleraesuis, S. choleraesuis, S. enterica, S. paratyphi, S. pullorum, S. subterranea*, and *S. typhi* or *Pseudomonas*, e.g; a bacterium of the *Pseudomonas aeruginosa* group such as *P. aeruginosa, P. alcaligenes, P. anguilliseptica, P. argentinensis, P. borbori, P. citronellolis, P. flavescens, P. mendocina, P. nitroreducens, P. oleovorans, P. pseudoalcaligenes, P. resinovorans* or *P. straminea*, or *Neisseria* sp., *Hemophilus* sp., *Proteus* sp., *Klebsiella* sp., *Escherichia coli* or other bacteria such as *Serratia liquefaciens, Burkholdeia cepacia, Porphyromonoas gingivalis* or yeasts such as *C. albicans*.

The compositions and methods of this inventions are also useful for reducing or eradicating a biofilm consisting of a combination of any one of the bacterial and/or yeast species as described above.

Yet another embodiment of present invention is a process for imparting microbial control properties to a fluid composition, said process comprising adding an antimicrobial composition as defined hereinabove to said fluid composition.

Examples

Materials and Methods

General Procedure for the Synthesis of N-Substituted 2-aminoimidazoles (Compounds 8).

As depicted in FIG. 2, the previously developed 2-Ais 7 (6) were further functionalized by reductive amination of the 2N-position of the 2-Als with isobutyraldehyde and cyclopentanone. The desired N1-,2N-disubstituted 5-Ar-2Ais 8 were obtained in moderate yields. These compounds combine the N1-octyl substituent of compound 2 with the 2N-isobutyl or 2N-cyclopentyl substituent of compounds 3 and 5 respectively.

To a solution of 2-aminoimidazole compound 7 (FIG. 2) (6) in toluene was added isobutyraldehyde or cylcopentanon (1.2 equiv). The mixture was stirred at 120° C. for 3 h. After cooling to rt the solvent was reduced in vacuo. The crude intermediate was dissolved in MeOH and cooled to 0° C. NaBH$_4$ (4 equiv) was added portion wise. The reaction was stirred for 16 h at rt. The solvent was reduced in vacuo, the crude product was taken up in water and extracted with ethyl acetate. The resulting organic phases were washed with brine, dried over sodium sulphate, filtered and concentrated in vacuo. The products were purified by chromatography over silica gel with ethyl acetate/heptane (7/3) as eluent.

N-isobutyl-1-octyl-5-phenyl-1H-imidazol-2-amine (8a)

Obtained from the general procedure as an orange oil, yield 57%. $^1$H NMR (300 MHz, Chloroform-d) δ 7.52-7.20 (m, 5H), 6.71 (s, 1H), 3.71 (t, J=7.5 Hz, 3H), 3.23 (t, J=6.4 Hz, 2H), 1.96 (dp, J=13.4, 6.7 Hz, 1H), 1.80-1.45 (m, 2H), 1.18 (s, 10H), 1.00 (d, J=6.6 Hz, 6H), 0.86 (t, J=6.8 Hz, 3H). $^{13}$C NMR (75 MHz, CDCl$_3$) δ 150.75, 131.13, 129.25, 128.67, 128.60, 128.23, 128.16, 127.05, 123.00, 51.56, 42.64, 31.67, 29.42, 29.02, 28.98, 28.94, 28.42, 26.51, 22.58, 20.32, 14.06.

5-(4-chlorophenyl)-N-isobutyl-1-octyl-1H-imidazol-2-amine (8b)

Obtained from the general procedure as an orange oil, yield 46%. $^1$H NMR (300 MHz, Chloroform-d) δ 7.37 (d, J=8.1 Hz, 2H), 7.17 (d, J=8.2 Hz, 2H), 6.69 (s, 1H), 3.79 (t, J=7.5 Hz, 2H), 3.16 (d, J=6.9 Hz, 2H), 1.98-1.81 (m, 1H), 1.48 (t, J=7.5 Hz, 2H), 1.32-1.03 (m, 10H), 0.95 (d, J=6.6 Hz, 6H), 0.85 (t, J=6.9 Hz, 3H). $^{13}$C NMR (75 MHz, CDCl3) δ 148.89, 134.47, 129.77, 129.11, 127.79, 127.32, 115.99, 51.07, 43.09, 31.61, 28.93, 28.84, 28.80, 28.50, 28.27, 26.15, 22.54, 22.52, 19.99, 14.02.

5-(4-bromophenyl)-N-isobutyl-1-octyl-1H-imidazol-2-amine (8c)

Obtained from the general procedure as a yellow oil, yield 52%. $^1$H NMR (300 MHz, Chloroform-d) δ 7.62-7.45 (m, 2H), 7.25-7.10 (m, 2H), 6.72 (s, 1H), 3.79-3.57 (m, 3H), 3.23 (t, J=6.3 Hz, 2H), 1.95 (dt, J=13.4, 6.7 Hz, 1H), 1.57 (t, J=7.5 Hz, 2H), 1.32-1.11 (m, 10H), 1.00 (d, J=6.6 Hz, 6H), 0.87 (t, J=6.8 Hz, 3H). $^{13}$C NMR (75 MHz, CDCl$_3$) δ 151.09, 131.78, 130.10, 129.54, 128.01, 123.68, 120.94, 51.50, 42.68, 31.68, 29.44, 29.03, 28.95, 28.41, 26.50, 22.60, 20.30, 14.07.

5-(3,4-dichlorophenyl)-N-isobutyl-1-octyl-1H-imidazol-2-amine (8d)

Obtained from the general procedure as an orange oil, yield 41%. $^1$H NMR (300 MHz, Chloroform-d) δ 7.43-7.28 (m, 2H), 7.06 (dt, J=8.3, 1.9 Hz, 1H), 6.56 (d, J=29.1 Hz, 1H), 4.12-3.53 (m, 3H), 3.54-2.88 (m, 1H), 1.78-1.47 (m, 2H), 1.29-0.96 (m, 12H), 0.96-0.86 (m, 4H), 0.86-0.64 (m, 4H). $^{13}$C NMR (75 MHz, CDCl$_3$) δ 151.41, 131.54, 130.64, 129.64, 129.11, 125.61, 124.79, 122.55, 41.74, 39.10, 30.63, 28.52, 28.12, 26.49, 25.61, 25.50, 22.86, 22.66, 21.56, 19.94, 16.61, 13.02.

N-cyclopentyl-1-octyl-5-phenyl-1H-imidazol-2-amine (8e)

Obtained from the general procedure as an orange oil, yield 67%. $^1$H NMR (300 MHz, Chloroform-d) δ 7.32 (tt, J=12.4, 7.3 Hz, 5H), 6.73 (s, 1H), 4.20 (q, J=6.3 Hz, 1H), 3.69 (t, J=7.6 Hz, 2H), 3.53 (d, J=6.1 Hz, 1H), 2.10 (tt, J=12.2, 5.0 Hz, 2H), 1.91-1.61 (m, 3H), 1.53 (dq, J=12.1, 6.3, 5.7 Hz, 4H), 1.39-1.05 (m, 10H), 0.86 (t, J=6.8 Hz, 3H). $^{13}$C NMR (75 MHz, CDCl$_3$) δ 150.40, 131.21, 129.06, 128.52, 128.08, 128.06, 126.90, 126.88, 123.28, 55.21, 42.51, 35.46, 33.71, 33.69, 31.63, 29.32, 28.96, 28.86, 26.37, 26.35, 23.73, 23.32, 22.55.

5-(4-chlorophenyl)-N-cyclopentyl-1-octyl-1H-imidazol-2-amine (8f)

Obtained from the general procedure as an orange oil, yield 41%. $^1$H NMR (300 MHz, Chloroform-d) δ 7.49-7.30 (m, 2H), 7.26 (d, J=3.9 Hz, 2H), 6.73 (s, 1H), 4.19 (q, J=6.2 Hz, 1H), 3.66 (t, J=7.6 Hz, 2H), 3.44 (d, J=6.2 Hz, 1H), 2.26-2.00 (m, 2H), 1.79-1.61 (m, 2H), 1.52 (ddd, J=12.6, 7.9, 5.4 Hz, 4H), 1.34-1.07 (m, 12H), 0.87 (t, J=6.8 Hz, 3H). $^{13}$C NMR (75 MHz, CDCl$_3$) δ 129.46, 128.93, 127.98, 55.40, 42.80, 33.72, 31.68, 29.25, 29.02, 28.90, 26.40, 23.76, 22.60, 14.07.

5-(4-bromophenyl)-N-cyclopentyl-1-octyl-1H-imidazol-2-amine (8g)

Obtained from the general procedure as an orange oil, yield 52%. $^1$H NMR (300 MHz, Chloroform-d) δ 7.52 (dd, J=8.5, 2.0 Hz, 2H), 7.20 (dd, J=8.4, 2.0 Hz, 2H), 6.75 (d, J=2.1 Hz, 1H), 4.20 (q, J=6.3 Hz, 1H), 3.67 (t, J=7.5 Hz, 2H), 3.44 (d, J=6.2 Hz, 1H), 2.27-1.98 (m, 2H), 1.94-1.62 (m, 4H), 1.53 (dq, J=11.6, 5.7 Hz, 4H), 1.19 (s, 10H), 0.88 (t, J=6.5 Hz, 3H). $^{13}$C NMR (75 MHz, CDCl$_3$) δ 131.79, 130.13, 129.56, 127.96, 123.82, 120.96, 55.29, 42.66, 33.81, 31.69, 29.42, 29.03, 28.92, 26.46, 23.75, 22.61, 14.08.

5-(3,4-dichlorophenyl)-N-cyclopentyl-1-octyl-1H-imidazol-2-amine (8h)

Obtained from the general procedure as a yellow oil, yield 49%. $^1$H NMR (300 MHz, Chloroform-d) δ 7.49-7.36 (m, 2H), 7.14 (dd, =8.3, 2.1 Hz, 1H), 6.76 (s, 1H), 4.19 (q, J=6.3 Hz, 1H), 3.80-3.57 (m, 2H), 3.50 (d, J=6.2 Hz, 1H), 2.22-1.98 (m, 2H), 1.80-1.61 (m, 4H), 1.60-1.43 (m, 4H), 1.19 (d, J=3.1 Hz, 10H), 0.87 (t, J=6.8 Hz, 3H). $^{13}$C NMR (75 MHz, CDCl$_3$) δ 151.06, 132.70, 131.31, 130.75, 130.58, 129.29, 126.93, 126.78, 124.82, 55.27, 42.74, 33.79, 31.68, 29.42, 29.04, 28.91, 26.43, 23.74, 22.60, 14.07.

Chemistry: Reagents and Analysis.

All solvents and reagents were purchased from commercial sources and were used without prior purification. TLC analysis was performed on aluminium backed plates. The products were purified by silica gel (200-300 mesh) column chromatography. All NMR spectra were recorded on a Bruker Avance 300 spectrometer at 300 MHz ($^1$H) and at 75 MHz ($^{13}$C). The $^1$H and $^{13}$C chemical shifts are reported in parts per million relative to tetramethylsilane using the residual solvent signal as the internal reference. The following abbreviation were used to designate chemical shift multiplicities: s=singlet, d=doublet, dd=doublet of doublets, t=triplet, dt=doublet of triplets, q=quartet, p=pentet and m=multiplet. The $^{13}$C NMR spectra are proton decoupled. 2-Aminoimidazoles 1-7 were synthesized according to established literature procedures [17-19][14].

Strains and Growth Media.

The strains P. aeruginosa PA14 [16], Escherichia coli TG1 (16), E. coli MG1655 (17), S. enterica serovar typhimurium ATCC14028 (18), Porphyromonas gingivalis ATCC33277 (20), Serratia liquefaciens MG44 [21], Burkholderia cepacia LMG1222T (20), C. albicans SC5314 (21), Staphylococcus aureus ATCC6538, S. aureus SH1000 [24,25] and Staphylococcus epidermidis [26] were used in this study. Overnight cultures of C. albicans SC5314 were grown with aeration in YPD (1% yeast extract, 2% peptone, and 2% dextrose) at 30° C. Overnight cultures of E. coli TG1, S. typhimurium ATCC14028, S. liquefaciens MG44, B. cepocia LMG1222T, S. aureus ATCC6538, S. aureus SH1000 and S. epidermidis were grown with aeration in lysogeny broth (LB) at 37° C. (16). For the experiments on the coated titanium substrates, overnight cultures of S. aureus SH1000 were grown in Tryptic Soy Broth (TSB) at 37° C. in shaking conditions. Overnight cultures of P. gingivalis ATCC33277 were grown anaerobically (Anoxomat, AN20®; Mart Microbiology, Drachten, the Netherlands) in LB at 37° C. Overnight cultures of P. aeruginosa PA14 were grown with aeration in LB or in Trypticase soy broth (TSB) at 37° C. Overnight cultures of E. coli MG1655 were grown with aeration in TSB at 37° C. Phosphate-buffered saline (PBS) was prepared by combining 8.8 g liter$^{-1}$ NaCl, 1.24 g liter$^{-1}$ K$_2$HPO$_4$, and 0.39 g liter$^{-1}$ KH$_2$PO$_4$ (pH 7.4). RPMI 1640 medium with L-glutamine and without sodium bicarbonate was purchased from Sigma and buffered to pH 7.0 with MOPS (morpholinepropanesulfonic acid; Sigma, St. Louis, Mo.) (final concentration, 165 mM).

Anti-Biofilm Assay: Inhibition of Bacterial Biofilms.

A static peg assay, described previously [7,27], was used for bacterial biofilm formation. The Calgary Biofilm Device consists of a platform carrying 96 polystyrene pegs (Nunc no. 445497) that fits as a microtiter plate lid with one peg hanging into each microtiter plate well (Nunc no. 269789). Twofold serial dilutions of the compounds (dissolved in 100% DMSO or ethanol) in 100 µl liquid broth (TSB diluted 1/20) per well were prepared in the microtiter plate in duplicate or triplicate, with a maximum concentration of 1600 µM and a minimum concentration of 0.8 µM. Subsequently, an overnight culture of S. typhimurium ATCC14028, P. aeruginosa PA14, E. coli TG1, S. aureus SH1000 or S. aureus ATCC6538 (all grown in LB) was diluted 1:100 into TSB 1/20 (or TSB for S. aureus SH1000), whereas overnight cultures of S. liquefociens MG44 and B. cepacia LMG1222T were diluted 1:50 into TSB 1/20. P. gingivalis ATCC33277 cultures were diluted in TSB 1/20 to have a final concentration of 1·10$^8$ cells/ml. Next 100 µl was added to each well of the microtiter plate, resulting in a total volume of 200 µl medium per well (final concentration of compounds ranges from 800 µM (2% DMSO or ethanol) to 0.4 µM (0.001% DMSO or ethanol). In the next step, the pegged lid was placed on the microtiter plate and the plate was incubated for 24 h or 48 h at 25° C. or 37° C. without shaking. At 37° C. the plates were placed in a sealed container with wet towels on the bottom to prevent evaporation of the growth medium. Biofilms of P. gingivalis ATCC33277 were grown anaerobically at 37° C. for 72 h. During this incubation period, biofilms were formed on the surface of the pegs. After incubation, the optical density at 600 nm (OD$_{600}$) was measured for the planktonic cells in the microtiter plate using a Synergy MX multimode reader (Biotek, Winooski, Vt.). This gives a first indication of the effect of the compounds on the planktonic growth. For quantification of biofilm formation, the pegs were washed once in 200 µl PBS. The remaining attached bacteria were stained for 30 min with 200 µl 0.1% (w/v) crystal violet in an isopropanol/methanol/PBS solution (v/v 1:1:18). Excess stain was rinsed off by placing the pegs in a 96-well plate filled with 200 µl distilled water per well. After air drying the pegs (30 min), the dye bound to the adherent biofilm was extracted with 30% glacial acetic acid (200 µl per well of a 96-well plate). The optical densities at 570 nm (OD$_{570}$) of each well was measured using a Synergy MX multimode reader (Biotek, Winooski, Vt.). The BIC$_{50}$ and IC$_{50}$ values for each compound were determined from the concentration gradient by using nonlinear curve fitting (GraphPad Prism 5; Graphpad Software, Inc., La Jolla, Calif.). $BIC_{50}$ is defined as the concentration of compound needed to inhibit biofilm formation by 50%. In the same assay the effect on planktonic growth was evaluated. $IC_{50}$ is defined as the concentration of compound needed to inhibit planktonic growth by 50%. The activity is considered biofilm-specific if the $BIC_{50}$ is at least two times lower than the $IC_{50}$. Data represent the means of at least 3 technical repeats with the corresponding 95% confidence intervals.

Anti-Biofilm Assay: Inhibition of C. albicans Biofilms

The potential of the compounds to prevent C. albicans SC5314 biofilm formation was assessed using the cell titer blue (CTB) quantification method (26). For the CTB method, an overnight culture of C. albicans SC5314 was washed with PBS and a cell suspension of $10^6$ cells/ml ($OD_{600}$=0.1) was prepared in RPMI 1640 medium (pH 7.0). Twofold serial dilutions of the compounds (dissolved in 100% DMSO or ethanol) in 100 µl RPMI 1640 medium per well were prepared in a round-bottomed polystyrene 96-well microtiter plate (TPP; Trasadingen, Switzerland) in duplicate or triplicate, with a maximum concentration of 1600 µM and a minimum concentration of 0.8 µM. 100 µl of the cell suspension was added to each well of the microtiter plate, resulting in a total volume of 200 µl medium per well (final concentration of compounds ranges from 800 µM (2% DMSO or ethanol) to 0.4 µM (0.001% DMSO or ethanol). After 16 h of static incubation at 37° C., biofilms were washed and quantified with CTB as described previously [26].

Mixed Biofilm Assays.

C. albicans/E. coli Biofilms.

Overnight cultures of C. albicans SC5314 (YPD) and E. coli MG1655 (TSB). were washed three times with PBS, after which they were diluted in RPMI medium to optical densities at 600 nm ($OD_{600}$) of 1 and 0.01, respectively. Equal volumes of these cell suspensions were mixed, and 100 µl of this mixed cell suspension together with compound was added to the wells of a microtiter plate in triplicate. The concentrations 25 µM (0.0625% DMSO or ethanol) and 100 µM (0.25% DMSO or ethanol) were tested. After 24 h incubation at 37° C. the medium was removed and the biofilm was washed with PBS. Next, the cells were re-suspended in 100 µl of PBS by scraping off, sonication (1 min, 45 kHz, USC300-T; VWR, Radnor, Pa., USA) and vigorously pipetting up-and-down. Finally, dilution series were made, and quantification of E. coli MG1655 and C. albicans SC5314 populations was performed using selective plating on TSA plates containing 25 mg/L amphotericin B and YPD plates containing 100 µg/ml tetracycline, respectively. The percentage of C. albicans SC5314 and E. coli MG1655 cells was determined relative to the DMSO or ethanol control treatment.

C. albicans/S. epidermidis Biofilms.

Overnight cultures of C. albicans SC5314 (YPD) and S. epidermidis (TSB) were diluted in RPMI 1640 medium to $OD_{500}$ of 0.05 and 0.01, respectively. Equal volumes of the cell suspensions of each organism were mixed before use. 100 µl of this mixed cell suspension together with compound was added to the wells of a round-bottom microtiter plate (TPP, Trasadingen, Switzerland) in triplicate. The concentrations 25 µM (0.0625% DMSO or ethanol) and 100 µM (0.25% DMSO or ethanol) were tested. After 24 h of incubation at 37° C., biofilms were washed with PBS and fresh medium with or without compounds was added. After further incubation for 48 h at 37° C., the biofilms were washed with PBS after which the cells were re-suspended in 100 µl of PBS by scraping off, sonication (1 min, 45 kHz, USC300-T; VWR, Radnor, Pa., USA) and vigorously pipetting up-and-down. Finally, the biofilm cells were diluted in PBS and plated on YPD agar plates containing 100 mg/L ampicillin and TSA plates containing 25 mg/L amphotericin B, to determine the number of fungal and bacterial CFUs after 2 days of incubation at 37° C., respectively. The percentage of C. albicans SC5314 and S. epidermidis cells was determined relative to the DMSO or ethanol control treatment.

C. albicans/S. aureus Biofilms.

Overnight cultures of C. albicans SC5314 (YPD, 30° C.) and S. aureus SH1000 (LB, 37° C.) were washed with PBS, after which they were diluted in RPMI medium to obtain cell suspensions of $10^6$ cells/ml for fungal cells and $10^8$ cells/ml for bacteria. Equal volumes of these cell suspensions were mixed, and 100 µl of this mixed cell suspension together with compound was added to the wells of a microtiter plate in triplicate. The concentrations 25 µM (0.0625% DMSO or ethanol) and 100 µM (0.25% DMSO or ethanol) were tested. The plates were incubated at 37° C. for 90 min. After incubation the wells were washed twice with PBS, and 200 µl of the fresh RPMI medium with or without compounds was added in triplicate to the wells. After 24 h incubation at 37° C. the medium was removed and the biofilm was washed with PBS. Next, the cells were re-suspended in 100 µl of PBS by scraping off, sonication (1 min, 45 kHz, USC300-T; VWR, Radnor, Pa., USA) and vigorously pipetting up-and-down. Finally, dilution series were made, and quantification of S. aureus SH1000 and C. albicans SC5314 populations was performed using selective plating on TSA plates containing 25 mg/L amphotericin B and YPD plates containing 100 µg/ml tetracycline, respectively. The percentage of C. albicans SC5314 and S. aureus SH1000 cells was determined relative to the DMSO or ethanol control treatment.

E. coli/P. aeruginosa Biofilms.

Overnight cultures of E. coli TG1 and P. aeruginosa PA14, were diluted 1/100 in the same vial of TSB 1/20 to form a mixed culture suspension. Next twofold serial dilutions of the compounds (dissolved in 100% DMSO or ethanol) in 100 µl liquid broth (TSB diluted 1/20) per well were prepared in the microtiter plate of the Calgary Biofilm Device (Nunc no. 269789) in duplicate or triplicate, with a maximum concentration of 1600 µM and a minimum concentration of 0.8 µM. 100 µl of the mixed culture suspension was added to each well of the microtiter plate, resulting in a total volume of 200 µl medium per well (final concentration of compounds ranges from 800 µM (2% DMSO or ethanol) to 0.4 µM (0.001% DMSO or ethanol). The pegged lid was placed on the microtiter plate, and the plate was incubated for 72 h at 37° C., which allowed biofilm formation on the pegs (Nunc no. 269789) of the Calgary Biofilm Device. After 72 h, the biofilm was colored with crystal violet as described above [27]. $OD_{570}$ (biofilm) and $OD_{600}$ (planktonic) were measured and $BIC_{50}$ as well as $IC_{50}$ were calculated, respectively.

S. aureus/S. epidermidis Biofilms.

Overnight cultures of S. aureus ATCC6538 and S. epidermidis were grown in LB medium and were diluted 1/200 in the same vial of TSB to form a mixed culture suspension. Next twofold serial dilutions of the compounds (dissolved in 100% DMSO or ethanol) in 100 µl TSB medium per well were prepared in the microtiter plate (Nunc no. 269789) in duplicate or triplicate, with a maximum concentration of 1600 µM and a minimum concentration of 0.8 µM. 100 µl of the mixed culture suspension was added to each well of the microtiter plate, resulting in a total volume of 200 µl medium per well (final concentration of compounds ranges from 800 µM (2% DMSO or ethanol) to 0.4 µM (0.001% DMSO or ethanol). Cells were then incubated for 48 h at 37° C., which allowed biofilm formation on the pegs (Nunc no. 269789) of the Calgary Biofilm Device. After 24 h fresh medium with compounds was added to the wells, and after 48 h the biofilm was colored with crystal violet as described above [27]. $OD_{570}$ (biofilm) and $OD_{600}$ (planktonic) were measured and $BIC_{50}$ as well as $IC_{50}$ were calculated respectively.

Mammalian-Cell Viability Assay.

Cell viability of two human primary cell types, namely, osteoblasts (OB) and bone-marrow derived mesenchymal stem cells (MSC) was tested according to the ISO 10993-5 standard, as previously described [29]. Briefly, cells were seeded in 96-well tissue culture test plates (TPP, Switzerland) at $5 \times 10^3$ cells/$cm^2$ in Advanced DMEM cell culture media supplemented with 10% serum, 1× GlutaMAX, 0.05 mg/mL Gentamycin, and were allowed to attach overnight. The next day, the cells were exposed to (i) cell culture medium and medium with the corresponding control (0.5% ethanol or DMSO) (negative controls), (ii) medium with 0.05% phenol (cytotoxic control), and (iii) medium with compounds (12.5 µM) and incubated for 2 h, 48 h and 6 days (8 repeats for each condition). At each time-point the numbers of viable and dead cells were determined directly by trypan blue staining, and indirectly by measuring the metabolic activity with MTT (3-(4,5-dimethylthiazol-2-yl)-2,5-diphenyltetrazolium bromide) staining.

Trypan Blue Staining.

The medium was removed from the wells, and 1/3 trypan blue in Dulbecco's modified Eagle's medium (DMEM) was added to the cells, incubated for 3 min, after which trypan blue was removed and DMEM medium was added to the wells. In each of four wells, two microscopy fields were counted for viable (transparent) and dead (blue) cells.

MTT Staining.

The medium was removed from the wells and 100 µl of medium, supplemented with 10% serum and 0.5 mg/mL MTT was added to the cells. The cells were incubated overnight at 37° C. and 5% $CO_2$. The next day the medium with MTT was removed and 100 µl acidic isopropanol was added. The cells were then centrifuged at 2300 g and 50 µl of the supernatant was transferred to a new 96-well plate. The absorbance was measured at 570 nm and the background was measured at 660 nm. Four wells per condition were examined.

Osteogenic Differentiation.

The effect on osteogenic differentiation potential was assessed as previously described [29]. Only the substances that allowed survival of the cells for more than 3 weeks, which is the time needed for mature osteogenic differentiation, were tested. Briefly, osteoblasts and bone-marrow derived mesenchymal stem cells were cultured in a positive solvent control (osteogenic medium with 0.5% DMSO or ethanol background), a negative control (medium without osteogenic supplements) and treated samples (osteogenic medium, 0.5% DMSO or ethanol background and 12.5 µM of test compound) with four repeats per condition. Mesenchymal stem cells and osteoblast cell cultures were harvested after 3 or 5 weeks, respectively, for the calcium and DNA assay.

Calcium and DNA Assay.

Calcium deposition of osteoblasts and mesenchymal stem cells was measured with the Calcium CPC LiquiColor test (Stanbio Laboratory, Boerne, Tex.) as previously described [29]. Briefly, cell cultures were extracted with 5% trichloroacetic acid (500 µl per sample), O-cresolphtalein complex was added, and the calcium content was determined spectrophotometrically at 550 nm. DNA content was determined as previously described [29]. DNA values were used to normalize the calcium content. Four wells per condition were examined, and two samples from each well were taken for each assay.

Covalent Attachment of Functionalized 2-aminoimidazoles on Titanium Substrates.

Figure 6A:
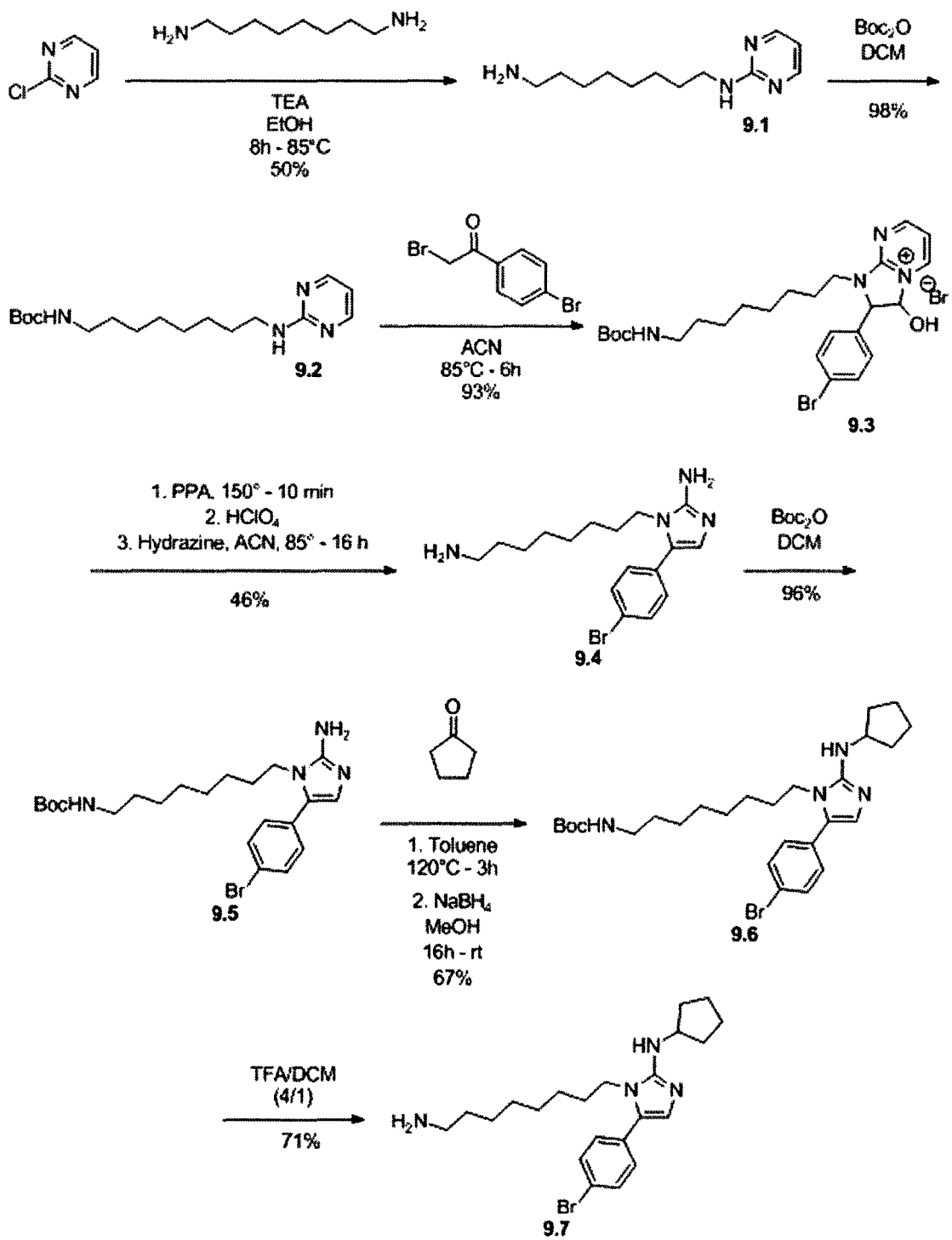
FIG. 6 Schematic representation of the covalent attachment of functionalized 2-aminoimidazoles on titanium substrates. A. Synthesis of a LC0024 (8 g) analogue containing a primary amine (LC0024-NH2 or 9.7). B. Coupling of LC0024-NH2 to functionalized titanium surface.

To enhance osseointegration potential, sterile round Ti discs (commercially pure Ti, grade 2; height: 2 mm; diameter: 5 mm) were first roughened by bead blasting with high purity $Al_2O_3$ particles and by etching using an acid mixture, followed by a washing step with isopropanol. The roughness of the discs, received from Biotech Dental (Salon-de-Provence, France), was determined with white light interferometry (Wyko NT 3300 Optical Profiler, Veeco Instruments, Mannheim, Germany), which resulted in an average surface roughness, $S_a$, of 0.78±0.14 µm; a ten point height, $S_z$, of 8.18±1.56 µm and a root mean square roughness, $S_q$, of 0.98±0.18. These smooth Ti discs were next functionalized with a carboxylic acid moiety by treatment with Fmoc-protected 3-aminopropyl-triethoxy silane, followed by deprotection with tetrahydrofuran/piperidine (90:10) (30). Subsequently, the functionalized Ti discs were placed in a hydrolysis vessel containing a n-heptane/hexamethylene diisocyanate (85:15) solution (1 mL/disc), were agitated for 3 h at room temperature and then rinsed with n-heptane. Next, the discs were transferred to a 6-aminohexanoic acid solution, were agitated for 16 h and rinsed with demineralized, pyrogen-free water and afterwards with acetone. The rinsed samples were then dried at room temperature for 1 h. For covalent attachment of LC0024 (compound 8g from FIG. 2) to the Ti discs, a LC0024 analogue containing a primary amine was synthesized (LC0024-$NH_2$). (FIG. 6A, compound 9.7), according to a method based on the method described in reference 6 and the method described above for synthesis of compounds 8. The detailed synthesis protocol is provided below and in FIG. 6A.

N1-(pyrimidin-2-yl)octane-2,8-diamine (9.1)

To a solution of 2-chloropyrimidine (5 g, 43.7 mmol) in Ethanol (50 ml) is added octane-1,8-diamine (18.9 g, 131 mmol, 3 equiv). The reaction is stirred at 85° C. for 16 h. After cooling down to room temperature the solvent is removed in vacuo. The crude is taken up into ethyl acetate (40 mL) and washed with water (2×20 mL). The organic layer is dried over $Na_2SO_4$, filtered and reduced in vacuo. The crude is purified by chromatography over silica gel with DCM/MeOH/TEA (100/10/2) as eluent. The product is isolated a yellow oil (4.8 g, 50%).

$^1$H NMR (300 MHz, Chloroform-d) δ 8.27 (d, J=4.8 Hz, 2H), 6.50 (t, J=4.8 Hz, 1H), 5.43 (s, 2H), 3.39 (td, J=7.2, 5.7 Hz, 2H), 2.67 (t, I=6.9 Hz, 2H), 1.68-1.50 (m, 2H), 1.54-1.22 (m, 11H). $^{13}$C NMR (75 MHz, $CDCl_3$) δ 162.42, 157.96, 110.18, 42.23, 41.43, 33.83, 29.53, 29.39, 29.31, 26.88, 26.79.

Tert-butyl (8-(pyrimidin-2-ylamino)octyl)carbamate (9.2)

To a solution of N1-(pyrimidin-2-yl)octane-1,8-diamine (4.8 g, 21.6 mmol) in DCM (50 mL) is added di-tert-butyl dicarbonate (4.7 g, 21.6 mmol). The reaction is stirred overnight at rt. Afterwards the volatiles were removed in vacuo. The product was isolated a yellow oil (6.8 g, 98%) and used without further purification.

$^1$H NMR (300 MHz, Chloroform-d) δ 8.27 (d, J=4.8 Hz, 2H), 6.50 (t, J=4.8 Hz, 1H), 5.27 (br, 1H), 4.56 (br, 1H), 3.39 (td, J=7.1, 5.8 Hz, 2H), 3.10 (q, J=6.9 Hz, 2H), 1.60 (ddd, J=14.3, 7.9, 6.3 Hz, 2H), 1.50-1.22 (m, 19H).

3-(4-bromophenyl)-1-(8-((tert-butoxycarbonyl) amino)octyl)-2-hydroxy-2,3-dihydro-1H-imidazo[1, 2-a]pyrimidin-4-ium bromide (9.3)

To a solution of tert-butyl (8-(pyrimidin-2-ylamino)octyl) carbamate (6.8 g, 21. mmol) in ACN (75 mL) is added 2-bromo-1-(4-bromophenyl)ethan-1-one (7.62 g, 27.4 mmol). The reaction is stirred for 6 h at 85° C. After cooling to down to room temperature the volatiles were removed in vacuo and the crude product (11.8 g, 93%) is used for the next step.

1-(8-aminooctyl)-5-(4-bromophenyl)-1H-imidazol-2-amine (9.4)

To finely powdered 3-(4-bromophenyl)-1-(8-((tert-butoxycarbonyl)amino)octyl)-2-hydroxy-2,3-dihydro-1H-imidazo[1,2-a]pyrimidin-4-ium bromide (12 g, 19.99 mmol) in a beaker is added PPA (20 g). The mixture is heated to 150° C. while stirring with a glass rod until evaporation of water ceased. The suspension was cooled down to 60° C. and poured into 200 mL of ice water. After cooling to rt HClO4 (15%, 100 mL) was carefully added. The suspension was extracted using ethyl acetate (5×100 mL). The combined organic layers were washed with brine, dried over NaSO4 and filtered. The solvents were reduced in vacuo and the product was isolated as a yellow solid. The crude intermediate was used without further purification. To a solution of crude intermediate in ACN (30 mL) is added hydrazine (64% in water) (6.86 ml, 140 mmol). The reaction was stirred at 85° C. overnight. The solvent was reduced in vacuo. Hydrazine was removed by co-destillation with toluene (3×20 mL) in vauco. The crude product was purified by column chromatography over silica gel with ethyl acetate/ NH3 (7N in MeOH) 100/12 as eluent. The product was obtained an orange oil (3.34 g, 46%).

$^1$H NMR (300 MHz, Chloroform-d) δ 7.59-7.47 (m, 2H), 7.23-7.11 (m, 2H), 6.64 (s, 1H), 3.80-3.64 (m, 2H), 3.45 (s, 2H), 2.66 (t, J=7.0 Hz, 2H), 1.56 (t, J=7.5 Hz, 2H), 1.38 (q, J=7.0, 6.6 Hz, 2H), 1.19 (q, J=5.1, 4.3 Hz, 9H). $^{13}$C NMR (75 MHz, CDCl$_3$) δ 149.29, 131.84, 129.97, 129.65, 128.23, 123.43, 121.23, 50.27, 43.12, 42.02, 33.42, 29.46, 29.14, 28.86, 26.66, 26.33.

Tert-butyl (8-(2-amino-5-(4-bromophenyl)-1H-imidazol-1-yl)octyl)carbamate (9.5)

To a mixture of 1-(8-aminooctyl)-5-(4-bromophenyl)-1H-imidazol-2-amine (2 g, 5.47 mmol) in DCM (15 mL) is added di-tert-butyl dicarbonate (1.25 g, 5.75 mmol). The reaction is stirred overnight and afterwards the volatiles are removed in vacuo. The product (2.45 g, 96%) is used in the next step without further purification.

$^1$H NMR (300 MHz, Chloroform-d) δ 7.57-7.48 (m, 2H), 7.22-7.15 (m, 2H), 6.67 (s, 1H), 4.57 (s, 1H), 3.78-3.68 (m, 2H), 3.08 (q, J=6.6 Hz, 2H), 1.56 (t, J=7.4 Hz, 2H), 1.44 (s, 11H), 1.19 (t, J=6.9 Hz, 8H). $^{13}$C NMR (75 MHz, CDCl$_3$) δ 159.63, 149.18, 131.85, 129.63, 128.31, 123.78, 121.18, 50.87, 43.14, 29.50, 28.93, 28.83, 28.44, 26.55, 26.32.

Tert-butyl (8-(5-(4-bromophenyl)-2-(cyclopentylamino)-1H-imidazol-1-yl)octyl)carbamate (9.6)

To a suspension of tert-butyl (8-(2-amino-5-(4-bromophenyl)-1H-imidazol-1-yl)octyl)carbamate (2 g, 4.3 mmol) in toluene (25 mL) is added cyclopentanone (0.54 g, 6.45 mmol). The reaction is refluxed for 16 h and after cooling down to room temperature the solvent is removed in vacuo. Methanol (30 mL) is added and sodium borohydride (0.82 g, 21.5 mmol) is portion wise added at 0° C. The reaction is stirred for 16 h at rt. Afterwards MeOH is removed in vacuo and the crude is taken up in ethyl acetate (20 mL) and water (20 mL). The mixture is stirred for 15 min, separated and the water phase is extracted with ethyl acetate (2×20 mL). The combined organic layers are washed with brine (20 mL), dried over Na2SO4, filtered and reduced in vacuo. The crude product is purified by column chromatography over silica gel with ethyl acetate/TEA (100/5) as eluent. The product (1.53 g, 67%) is obtained as a yellow oil.

$^1$H NMR (300 MHz, Chloroform-d) δ 7.55-7.46 (m, 2H), 7.24-7.12 (m, 2H), 6.73 (s, 1H), 4.49 (5, 1H), 4.24-4.15 (m, 1H), 3.71-3.63 (m, 2H), 3.44 (d, J=6.2 Hz, 1H), 3.08 (q, J=6.7 Hz, 2H), 2.15-2.06 (m, 2H), 1.83-1.64 (m, 6H), 1.60-1.49 (m, 5H), 1.44 (s, 9H), 1.17 (t, J=6.8 Hz, 7H).

1-(8-aminooctyl)-5-(4-bromophenyl)-N-cyclopentyl-1H-imidazol-2-amine (9.7)

To a solution of tert-butyl (8-(5-(4-bromophenyl)-2-(cyclopentylamino)-1H-imidazol-1-yl)octyl)carbamate (1.53 g, 2.87 mmol) in DCM (20 mL) at 0° C. is dropwise added TFA (5 mL). The reaction is stirred for 16 h at room temperature. The solvents are removed in vacuo and the crude is taken up in ethyl acetate (30 mL) and a saturated solution of NaHCO$_3$ is added until the pH=8. The phases are separated and the water layer is extracted with ethyl acetate (4×20 mL). The combined organic layers are washed with brine (20 mL), dried over Na2SO4 and filtered and reduced in vacuo. The crude is purified by column chromatography over silica gel with ethyl acetate/NH3 (7N in MeOH (100/15) as eluent. The product 3.11 (880 mg, 71%) is obtained as a yellow oil.

$^1$H NMR (300 MHz, Chloroform-d) δ 7.51 (d, J=8.5 Hz, 2H), 7.17 (d, J=8.4 Hz, 2H), 6.72 (s, 1H), 3.74-3.64 (m, 2H), 3.44 (s, 3H), 2.76 (d, J=7.3 Hz, 2H), 2.15-2.02 (m, 2H), 1.80-1.58 (m, 4H), 1.58-1.38 (m, 6H), 1.34-1.04 (m, 9H). 13C NMR (101 MHz, CDCl3) δ 150.57, 131.84, 131.80, 129.96, 129.62, 129.59, 128.05, 123.31, 121.11, 55.39, 42.68, 41.30, 33.74, 31.41, 30.92, 29.18, 28.94, 28.88, 28.70, 26.46, 26.24, 23.73. HRMS (EI): m/z calculated for C$_{22}$H$_{33}$BrN$_4$: 432.1889; found: 432.1887.

This primary amine (compound 9.7) was reacted with the carboxyl moiety on the Ti surface of the discs by 16 hours of shaking at room temperature (FIG. 6B). A combination of carbodiimide (3 equivalents) and Oxyma (2 equivalents were employed in a dichloromethane/dimethylformamide (95/5) solvent mixture) were used as coupling reagents. After completion of the reaction the solid supports were washed with a dichloromethane/dimethylformamide (50/50) mixture (5 times) and with dichloromethane (3 times). Finally, these solid supports were dried under an argon stream.

Bacterial Biofilm Formation on Titanium Discs.

The potential of bacteria to form biofilms on Ti discs was assessed by first incubating the control-Ti and LC0024-Ti discs overnight in Fetal Bovin Serum (FBS, Life Technologies, Europe) at 37° C. in a box with a sterile moist tissue to prevent evaporation. Afterwards the discs were washed in PBS to remove the excess serum. Next the discs were transferred to the wells of a 24-well plate with the rough side up and silicon tubes (9 mm OD×5 mm ID×15 mm L) (VWR International) were placed over the discs to exclude the sides and bottoms. Overnight cultures of *S. aureus* were diluted in TSB medium and 200 µL of a 1×10$^4$ cells/mL suspension was added to the wells. After static incubation of 24 h at 37° C. in a box with a sterile moist tissue the discs were washed with sterile PBS and transferred to 2 mL eppendorf tubes filled with 1 mL PBS. The tubes with the discs were vigorously vortexed for 1 min, sonicated for 10 min at 45,000 Hz in a water bath sonicator (VWR USC 300-T) and vortexed again for 1 min. The resulting bacterial suspensions were diluted and plated on TSB plates. After 24 h of incubation at 37° C., the CFU/mL was determined by plate counting.

*S. aureus* Biofilm Formation on Coated Discs for Visualization with Confocal Laser Scanning Microscopy (CLSM).

*S. aureus* SH1000 biofilms were grown on control-Ti and LC0024-Ti discs as described above, and were d for visualization using the LIVE/DEAD® BacLight™ stain (Molecular Probes, USA) following the manufacturer's instructions. The stained biofilms were analyzed using a CLSM (Leica TCS SPS, Heidelberg, Germany) in an inverted microscope configuration, with a HCX PL APO CS 63x/1.2 water-immersion objective. During CLSM visualization, 25 digital images were taken with X-Y scan a few µm above the surface plane. The thickness of the optical sections was 577 nm at full width half maximum and the image resolution was 2048×2048 pixels. The LIVE (SYTO® 9) and DEAD (propidium iodide) stains were excited by an argon (488 nm) and a HeNe (594 nm) laser, respectively. The obtained images were analyzed in MATLAB using an in-house developed software macro to calculate the area fractions of live and dead cells in a thin optical section close to the surface of the Ti-disc. This macro allows to automatically run large series of images by subtracting the background, removing artifacts smaller than 20 pixels and calculating the area covered by objects over a set intensity.

*S. aureus* Biofilm-Associated Infection Model in Mice.

All animal experiments were approved by the Animal Ethical Committee of the KU Leuven (project number P125/2011). The model is based on the subcutaneous implant of a substrate on the backside of mice, followed by infection with precise microbial doses at the implant site after 24 h. Eight-week-old pathogen-free female BALB/c mice weighting 20 g were used. Mice were housed in individually ventilated cages (4 mice/cage) and were allowed ad libitum access to sterile food and water. A day before surgery, all animals were immunosuppressed by addition of dexamethasone (0.4 mg/L) to the drinking water. The immune system was suppressed throughout the entire experiment. The day of surgery, the mice were anaesthetized intraperitoneally with a mixture of ketamine (Ketamine1000®; Pfizer, Puurs, Belgium) and medetomidine (Domitor®; Pfizer) (45 mg/kg ketamine and 0.6 mg/kg medetomidine). Once asleep, the lower back of the animals was shaved and disinfected with iodine isopropanol (1%). Prior to the incision, the skin was locally anaesthetized with xylocaine gel (2%, AstraZeneca, Zoetermeer, the Netherlands). Next, a small subcutaneous incision was made to create a space of 2 cm long and 1 cm wide for the implant of one disc. After implantation, the incision was closed with surgical staples, disinfected and locally anaesthetized with xylocaine gel. Reversion of the anaesthesia was performed by intraperitoneal injection of atipamezole (Antisedan®; Pfizer, 0.5 mg/kg for mice). 24 h after implantation of the discs, the mice were anaesthetized with a mixture of ketamine and medetomidine as indicated above and were inoculated with *S. aureus* SH1000. Hereto, a bacterial overnight culture was washed and resuspended in sterile saline (0.9%) to a concentration of 1×10$^8$ cells/mL. 100 µL of the bacterial inoculum was injected subcutaneously into the area around the disc. Anaesthesia was reversed with an intraperitoneal injection of atipamezole as mentioned above. After 4 days of biofilm formation, the mice were euthanized by cervical dislocation and the discs were explanted. The skin was disinfected first with 0.5% chlorhexidine in 70% alcohol before the discs were removed from under the subcutaneous tissue, which was collected in microcentrifuge tubes. Biofilm formation on the Ti discs was evaluated by CFU counts. Hereto, biofilms formed on the discs were washed twice with PBS, sonicated for 10 min in a water bath sonicator (Branson 2210) at 40,000 Hz and vortexed for 30 s in 1 mL PBS. Surrounding tissue samples were weighed and homogenized. The resulting bacterial suspensions (discs and surrounding tissue) were diluted and plated in duplicate on TSB agar plates. CFUs were counted after incubation of 24 h at 37° C.

Cytotoxicity Test for Cells on the Coated Titanium Discs: Direct Contact Test

Human bone marrow derived stromal cells (MSC) were seeded at cell density of 5000 cells/cm$^2$ in advanced Dulbecco's Modified Eagle Medium (Life Technologies, USA) supplemented with 10% FBS, 1× GlutaMAX, and 0.05 mg/mL gentamicin (Gibco, Carlsbad, Calif.). Cell cultures were maintained in 5% $CO_2$ at 37° C., until reaching 95% confluence. Cells were then trypsinized (Trypsin-EDTA, Sigma Aldrich), counted with hemacytometer, and used for the direct contact test. Cells of 4$^{th}$ passage were used for the experiments.

Each disc was placed into one well of a 6-well culture plate (TPP, Switzerland) and the MSC were seeded in the culture well at cell density 5000 cells/cm$^2$. Cell cultures were maintained in 5% $CO_2$ at 37° C. for 6 days. The area in the vicinity of the discs (where cell culture is in direct contact with lateral surface of the discs) was monitored for changes in cell culture morphology and zone of growth inhibition. Photographs of cell culture in the vicinity of discs were taken at day 1, 3, and 6. At day 6, cell cultures were also stained with MTT (3-(4,5-dimethylthiazol-2-yl)-2,5-diphenyltetrazolium bromide) for better visualization. Hereto, 10% of MTT (Sigma Aldrich) was added to the cell culture medium and incubated overnight at 37° C. The next day cells were inspected for viability (violet crystals determined viable cells) and were photographed. Non-cytotoxic and cytotoxic reference material was used for positive and negative control. Experiments were performed in triplicates.

In Vitro Osseointegration Potential Test.

The in vitro osseointegration potential of the LC0024-Ti discs was determined using human bone marrow derived stromal cells (MSC) and human microvascular endothelial cells (HMVEC). MSC and HMVEC were cultured in advanced Dulbecco's Modified Eagle Medium (Life Technologies, USA) supplemented with 10% FBS, 1× GlutaMAX, and 0.05 mg/mL gentamicin (Gibco, Carlsbad, Calif.), and medium 131 supplemented with Microvascular Growth Supplement (Life Technologies, USA), respectively. MSC and HMVEC were seeded at cell densities of 5000 cells/cm$^2$ and cultured in 5% $CO_2$ at 37° C. for one passage. After reaching 95% confluence, cells were trypsinized (Trypsin-EDTA, Sigma Aldrich) and counted with a hemocytometer. Cells of 4th passage were used for the experiments.

The discs were placed into the wells of a 24-well culture plate (TPP, Switzerland). Subsequently, the top areas of the discs were seeded with MSC or HMVEC at cell density 9000 cells/disc: approximately 50 µL of cell suspension was placed on the top of the disc, and distributed evenly so that a drop covered the whole area of the disc. Discs were then kept in the incubator, allowing cells to attach. After 30 min, additional culture medium was added. Cells were cultured for 5 and 12 days, and were then fixed with formalin for 15 min. Next, they were washed 3 times with PBS and incubated with phalloidin (for stock solution, 1 mg of phalloidin was dissolved in 10 ml methanol; for working solution, stock solution was diluted 1:20 with PBS) in the dark at room temperature for 30 min to stain the actin cytoskeleton. After incubation the cells were again washed 3 times with PBS and the samples were incubated with Vectashield/DAPI (Vector Laboratories, USA) to stain the nuclei. The smooth Ti discs were then imaged with a 40× objective on a fluorescent microscope (Nikon T300). Experiments were performed in triplicates.

Example 1. Preventive Activity of Selected 5-Ar-2AIs Against Bacterial and Fungal Biofilms We selected six 5-aryl-2-aminoimidazoles (5-Ar-2AIs) (FIG. 1) with previously reported activity against *S. typhimurium* (25° C.) and *P. aeruginosa* (25° C.) biofilms ($BIC_{50}$<75 µM) and tested their preventive anti-biofilm activity against a broad panel of bacterial and fungal pathogens in a monospecies biofilm setup, by using a crystal violet and CTB based assay, respectively (Table 1). $BIC_{50}$ is defined as the concentration of compound needed to inhibit biofilm formation by 50%. In the same assay the effect on planktonic growth was evaluated. $IC_{50}$ is defined as the concentration of compound needed to inhibit planktonic growth by 50%. The activity is considered biofilm-specific if the $BIC_{50}$ is at least two times lower than the $IC_{50}$. Our bacterial test panel included *S. liquefaciens* (Gram-negative γ-proteobacteria) capable of colonizing a wide variety of surfaces in water, soil, the digestive tracts of rodents, plants, insects, fish, and humans (nosocomial infections); *E. coli* (Gram-negative γ-proteobacteria), known to form biofilms on i.a. plant material, food (contact) surfaces and urinary catheters; *P. gingivalis* (Gram-negative bacteroidetes), an important constituent in dental plaque biofilms involved in periodontal diseases; *S. aureus* (Gram-positive cocci), which forms biofilms on i.a. chronic wounds and catheters and *B. cepacia* (Gram-negative (3-proteobacteria), involved in biofilm infections in the lungs of cystic fibrosis patients; next to the previously tested bacteria *S. typhimurium* and *P. aeruginosa* (Gram-negative γ-proteobacteria).

Compounds 1 and 2 are substituted at the N1-position of the 2-aminoimidazole moiety (39) with an alkyl group of intermediate length (FIG. 1) [32]. As indicated in Table 1, compound 2 was found to be very active against biofilm formation of the Gram-positive bacteria (*S. aureus* ATCC6538, *S. aureus* SH1000 and *S. epidermidis*) with $BIC_{50}$ values between 2 and 6 µM. Compound 1 also had an anti-biofilm activity against these bacteria, however, to a more moderate extent. Furthermore, both compounds showed potent and specific anti-biofilm activity against the Gram-negatives *P. gingivalis, P. aeruginosa* (25° C.), and *S. typhimurium*, with $BIC_{50}$ values between 2 and 50 µM. Both compounds also inhibited biofilm formation of *E. coli* and *P. aeruginosa* at 37° C. ($BIC_{50}$ between 6 and 120 µM), however, in a non-biofilm-specific way. Compound 2, but not compound 1, had potent biofilm-specific activity against *S. liquefaciens* biofilms ($BIC_{50}$=18.8 µM, $IC_{50}$=38.0 µM). Finally, both compounds moderately affected biofilm formation of *B. cepacia*, with $BIC_{50}$ values between 145 and 400 µM. Finally, compound 2 had a very strong capacity to inhibit biofilm formation of the fungus *C. albicans* ($BIC_{50}$=6.2 µM), while compound 1 was only moderately active.

The 2N-substituted 2-aminoimidazoles 3 to 5 (7) in general only showed a moderate, non-biofilm-specific activity against the Gram-positive bacteria *S. aureus* ATCC6538 and *S. aureus* SH1000 ($BIC_{50}$ values between 12.3 and 200.3 µM) while the compounds were not active against *S. epidermidis*. With respect to the Gram-negative species, a high activity was observed against *P. gingivalis, P. aeruginosa* (25° C.), *S. typhimurium*, and *S. liquefaciens* biofilms ($BIC_{50}$ values between 1 and 15 µM), a lower activity against *E. coli* and *B. cepacia* ($BIC_{50}$ values between 45 and 331 µM) and no activity against *P. aeruginosa* at 37° C. Only moderate activities were measured against the fungus *C. albicans*.

Finally, the 2-aminoimidazole/triazole conjugate 6 (13) displayed a potent, though non-biofilm-specific, activity against *P. gingivalis* and *S. typhimurium* ($BIC_{50}$ of 18.1 and 2 µM resp.) and a moderate, biofilm-specific activity against *S. aureus* ATCC6538, *P. aeruginosa* (25° C.) and *S. liquefaciens*. No activity against was observed against *S. aureus* SH1000, *S. epidermidis, P. aeruginosa* (37° C.), *B. cepacia* and *C. albicans*.

TABLE 1

Effect of 5-Ar-2AIs on a panel of monospecies bacterial and fungal biofilms

| | S. aureus ATCC6538 37° C. | | | | S. aureus SH1000 37° C. | | | |
|---|---|---|---|---|---|---|---|---|
| compd | $BIC_{50}{}^a$ (µm) | 95% confidence interval for $BIC_{50}$ | $IC_{50}{}^b$ (µm) | 95% confidence interval for $IC_{50}$ | $BIC_{50}$ (µm) | 95% confidence interval for $BIC_{50}$ | $IC_{50}$ (µm) | 95% confidence interval for $IC_{50}$ |
| 1 | 59.3* | 25.1-140.3 | 231.3 | 220.0-243.2 | 162.7* | 112.1-236.6 | >400.0 | |
| 2 | 2.8* | 1.9-4.0 | 7.8 | 3.8-16.0 | 3.4* | 2.1-5.4 | 8.3 | 6.2-11.1 |
| 3 | 95.3 | 41.4-219.5 | ~96.1 | | ~200.3 | | ~175.4 | |
| 4 | ~12.3* | | 60.1 | 50.0-72.3 | 66.5 | 49.1-90.0 | 89.4 | 75.5-105.8 |
| 5 | 34.4 | 22.2-53.3 | 62.3 | 52.1-74.6 | 70.6 | 51.3-97.1 | 71.5 | 51.8-98.7 |
| 6 | 75.2* | 41.4-136.6 | >400.0 | | >400.0 | | >400.0 | |

TABLE 1-continued

Effect of 5-Ar-2Als on a panel of monospecies bacterial and fungal biofilms

| | S. epidermidis 37° C. | | | | P. gingivalis ATCC33277 37° C. | | | |
|---|---|---|---|---|---|---|---|---|
| compd | $BIC_{50}$ (μm) | 95% confidence interval for $BIC_{50}$ | $IC_{50}$ (μm) | 95% confidence interval for $IC_{50}$ | $BIC_{50}$ (μm) | 95% confidence interval for $BIC_{50}$ | $IC_{50}$ (μm) | 95% confidence interval for $IC_{50}$ |
| 1 | ~201.7[d] | | ~329.0 | | 13.2* | 9.0-19.2 | 32.1 | 12.3-83.2 |
| 2 | ~5.6* | | ~11.1 | | 3.9* | 3.2-4.6 | 6.0 | 2.3-15.3 |
| 3 | >400.0 | | 86.2 | 63.1-117.8 | 5.3 | 2.5-11.3 | 5.1 | 3.1-8.4 |
| 4 | >400.0 | | 54.4 | 38.0-77.7 | 3.7* | 2.0-6.8 | 8.2 | 5.4-12.3 |
| 5 | >400.0 | | 39.5 | 25.4-61.5 | 5.7 | 2.6-12.6 | 4.0 | 1.4-11.7 |
| 6 | >400.0 | | >400.0 | | 18.1 | 7.7-42.5 | 19.5 | 7.7-49.2 |

| | E. coli TG1 37° C. | | | |
|---|---|---|---|---|
| compd | $BIC_{50}$ (μm) | 95% confidence interval for $BIC_{50}$ | $IC_{50}$ (μm) | 95% confidence interval for $IC_{50}$ |
| 1 | ~47.8 | | 34.1 | 29.4-39.6 |
| 2 | ~6.5 | | 7.7 | 5.7-10.4 |
| 3 | 110.2 | 73.8-164.6 | 30.0 | 24.3-37.0 |
| 4 | 84.7 | 45.7-157.0 | 23.0 | 15.7-33.7 |
| 5 | ~45.7 | | 17.1 | 14.3-20.5 |
| 6 | ~192.5 | | 182.8 | 108.1-309.3 |

| | P. aeruginosa PA14 | | | | | | | |
|---|---|---|---|---|---|---|---|---|
| | 25° C.[c] | | | | 37° C.[c] | | | |
| compd | $BIC_{50}$ (μm) | 95% confidence interval for $BIC_{50}$ | $IC_{50}$ (μm) | 95% confidence interval for $IC_{50}$ | $BIC_{50}$ (μm) | 95% confidence interval for $BIC_{50}$ | $IC_{50}$ (μm) | 95% confidence interval for $IC_{50}$ |
| 1 | 2.1* | 1.2-3.7 | ♦ | | 104.4 | 55.8-195.3 | 45.2 | 36.3-56.1 |
| 2 | 4.0* | 3.0-5.2 | ♦ | | 118.4 | 57.8-242.5 | 10.0 | 8.0-12.6 |
| 3 | 0.9* | 0.5-1.8 | ♦ | | >400.0 | | >400.0 | |
| 4 | 9.8* | 6.8-14.1 | ♦ | | >400.0 | | >400.0 | |
| 5 | 13.5* | 9.0-20.5 | ♦ | | >400.0 | | >400.0 | |
| 6 | 71.6* | 21.8-234.8 | >400.0 | | >400.0 | | >400.0 | |

| | S. Typhimurium ATCC14028 25° C. | | | | S. liquefaciens MG44 25° C. | | | |
|---|---|---|---|---|---|---|---|---|
| compd | $BIC_{50}$ (μm) | 95% confidence interval for $BIC_{50}$ | $IC_{50}$ (μm) | 95% confidence interval for $IC_{50}$ | $BIC_{50}$ (μm) | 95% confidence interval for $BIC_{50}$ | $IC_{50}$ (μm) | 95% confidence interval for $IC_{50}$ |
| 1 | 48.4* | 37.5-62.4 | ♦ | | 167.9 | 115.1-244.8 | 177.0 | 127.3-246.2 |
| 2 | ~5.9* | | ♦ | | 18.8* | 14.2-24.9 | 38.0 | 26.8-54.0 |
| 3 | 2.0* | 1.6-2.5 | ♦ | | 10.4* | 8.7-12.6 | 154.0 | 116.4-203.8 |
| 4 | 7.1* | 3.7-13.9 | ♦ | | 4.4* | 3.7-5.3 | 118.4 | 88.0-159.3 |
| 5 | 4.4* | 4.0-4.8 | ♦ | | 8.8* | 6.7-11.7 | 125.4 | 92.8-169.3 |
| 6 | 2.0 | 1.4-2.9 | 2.4 | 0.9-6.3 | 63.3* | 16.2-246.9 | >400.0 | |

| | B. cepacia LMG1222T 25° C. | | | | C. albicans SC5314 37° C. | | |
|---|---|---|---|---|---|---|---|
| compd | $BIC_{50}$ (μm) | 95% confidence interval for $BIC_{50}$ | $IC_{50}$ (μm) | 95% confidence interval for $IC_{50}$ | $BIC_{50}$ (μm) | 95% confidence interval for $BIC_{50}$ | |
| 1 | ~356.3 | | >400.0 | | 145.4 | 130.8-161.6 | |
| 2 | 145.4* | 9.5-400.0 | >400.0 | | 6.2 | 5.1-7.4 | |
| 3 | 88.1* | 21.5-360.9 | >400.0 | | 93.9 | 80.1-110.2 | |
| 4 | 189.0* | 56.6-400.0 | >400.0 | | 66.7 | 56.0-79.4 | |

TABLE 1-continued

Effect of 5-Ar-2AIs on a panel of monospecies bacterial and fungal biofilms

| 5 | 331.0  | 84.4-400.0 | >400.0 |        | 64.0   | 57.2-71.8 |
|---|--------|------------|--------|--------|--------|-----------|
| 6 | >400.0 |            | >400.0 |        | >400.0 |           |

$^a$BIC$_{50}$: concentration of compound needed to inhibit biofilm formation by 50%.
$^b$IC$_{50}$: concentration of compound needed to inhibit planktonic growth by 50%.
$^c$Biofilm formation was studied at 25° C. and 37° C. to simulate environmental and in vivo conditions, respectively.
$^d$~: The B(IC)$_{50}$ values could not be accurately calculated due to the steepness of the curve.
♦ The effect on the planktonic growth has previously been determined by growth curve analysis [6,7,9].
Compounds that have a biofilm-specific activity (2 × BIC$_{50}$ < IC$_{50}$) are marked with asterisks (*).

Example 2. Preventive Activity of Diverse 5-Ar-2AIs Against Mixed Bacterial-Fungal Biofilms There is clear evidence that *C. albicans* interactions with bacteria play an important role in several human diseases. Within mixed biofilms bacteria interact preferably with hyphal *C. albicans* cells. An overview of bacteria-*Candida* interactions and their effect on fungal development is provided in (40). Moreover, bacterial-fungal interactions can change the susceptibility to antimicrobial treatment. Mixed biofilms of *S. aureus* and *C. albicans* cells for instance show enhanced resistance of *S. aureus* to vancomycin, an effect which is in part mediated by the *C. albicans* matrix. Therefore, we evaluated the compounds of FIG. 1 for preventive activity against a panel of mixed bacterial-fungal biofilms, consisting of pairwise combinations of *C. albicans* and *E. coli, S. epidermidis* and *S. aureus*.

As indicated in Table 2, the N1-substituted 5-Ar-2AI 2 seems to be the best suited compound for treatment of mixed fungal-bacterial biofilms, since it caused a strong reduction of each species in the mixed biofilms tested at a concentration of 100 μM. Biofilm formation of *C. albicans/S. epidermidis* was even completely inhibited at 25 μM.

TABLE 2

Effect of 5-Ar-2AIs on a panel of mixed bacterial-fungal biofilms

| | *C. albicans* SC5314 + *E. coli* MG1655 37° C. CFUs % survival | | | | *C. albicans* SC5314 + *S. epidermidis* 37° C. CFUs % survival | | | | *C. albicans* SC5314 + *S. aureus* SH1000 37° C. CFUs % survival | | | |
|---|---|---|---|---|---|---|---|---|---|---|---|---|
| | 25 μM | | 100 μM | | 25 μM | | 100 μM | | 25 μM | | 100 μM | |
| compd | C.a. | E. coli | C.a. | E. coli | C.a. | S.e. | C.a. | S.e. | C.a. | S.a. | C.a. | S.a. |
| 2 | 104.9 | 158.6 | 0.0* | 0.1* | <0.6* | 0.0* | <0.2* | 0.0* | 183.8 | 87.7 | 0.9* | 0.2* |
| 3 | 143.4 | 138.5 | 59.6* | 63.0* | 58.3* | 64.6* | 235.1 | 13.2* | 165.7 | 124.6 | 141.3 | 51.8* |
| 5 | 100.8 | 100.6 | 38.3* | 105.6* | 167.9 | 72.0 | 594.7 | 2.3* | 232.4 | 75.4 | 120.6 | 74.5* |

C.a.: *Candida albicans*;
S.e.: *Staphylococcus epidermidis*;
S.a.: *Staphylococcus aureus*.
Compounds with <75% CFU survival are marked with asterisks(*).

The 2N-substituted compound 3 had a moderate (incomplete inhibition) activity against the *C. albicans/E. coli* combination, the *C. albicans/S. epidermidis* combination and against *S. aureus* within the *C. albicans/S. aureus* combination. Finally, compound 5 had a strong activity (complete inhibition at 100 μM) against *S. epidermidis* in the *C. albicans/S. epidermidis* biofilm, but only a moderate activity against *C. albicans* in the *C. albicans/E. coli* combination and *S. aureus* in the *C. albicans/S. aureus* combination.

Example 3. Preventive Activity of Diverse 5-Ar-2AIs Against Mixed Species Bacterial Biofilms Recent reports indicate that mixed species bacterial biofilms can be more resistant to antimicrobial agents than single species biofilms (41-48). The community level resilience can for example be provided by one resistant species able to protect the whole community (42). Therefore we evaluated a subset of the compounds of FIG. 1 for preventive activity against a mixture of the Gram-negative bacteria E. coli and P. aeruginosa (which often co-occur in urinary tract infections) (49) and a mixture of the Gram-positive bacteria S. aureus and S. epidermidis, by using a crystal violet based assay (50).

As indicated in Table 3, all compounds tested showed a strong preventive activity both against the mixture of Gram-negative and the mixture of Gram-positive bacteria, with $BIC_{50}$ values of between 0.5 and 74.3 µM. Remarkably, the activity of the 2N-substituted compounds against the mixed species biofilms was higher than that against monospecies biofilms of the constituent species.

a class of non-toxic compounds with a broad spectrum preventive activity against Gram-positive bacteria (both in monospecies and mixed species biofilms) is currently missing. This activity profile is especially interesting for application in anti-biofilm coatings for orthopedic implants, given the fact that Staphylococci are most frequently associated with implant infections (51). We hypothesized that 5-Ar-2AIs substituted at both the N1- and 2N-position might combine the broad-spectrum activity (or at least the activity against Gram-positives) of the N1-substituted compounds, with the low toxicity of the 2N-substituted compounds. To test this hypothesis a series of eight N1-,2N-disubstituted 5-Ar-2AIs was synthesized and tested for activity against a broad panel of bacterial and fungal biofilms and for toxicity against bone cells.

TABLE 3

Effect of 5-Ar-2AIs on a panel of mixed E. coli/P. aeruginosa and S. aureus/S. epidermidis biofilms.

| | E. coli TG1 + P. aeruginosa PA14 37° C. | | | | S. aureus ATCC6538 + S. epidermidis 37° C. | | | |
|---|---|---|---|---|---|---|---|---|
| compd | $BIC_{50}{}^a$ (µm) | 95% confidence interval for $BIC_{50}$ | $IC_{50}{}^b$ (µm) | 95% confidence interval for $IC_{50}$ | $BIC_{50}$ (µm) | 95% confidence interval for $BIC_{50}$ | $IC_{50}$ (µm) | 95% confidence interval for $IC_{50}$ |
| 1 | 74.3 | 33.0-167.7 | 60.7 | 42.4-87.1 | 44.2* | 18.4-119.0 | ~356.5$^c$ | |
| 2 | 36.8 | 16.2-85.0 | 19.9 | 14.6-26.9 | ~7.2 | | ~9.9 | |
| 3 | 7.4* | 3.8-21.5 | >400.0 | | ~26.3* | | ~140.5 | |
| 4 | 17.8* | 12.7-58.2 | >400.0 | | 6.8* | 1.7-36.3 | ~117.7 | |
| 5 | 0.5* | 0.2-1.5 | >400.0 | | ~66.6 | | ~91.7 | |
| 6 | 34.6* | 17.9-68.5 | >400.0 | | 33.9* | 17.1-67.5 | ~391.6 | |

$^a BIC_{50}$: concentration of inhibitor needed to inhibit biofilm formation by 50%.
$^b IC_{50}$: concentration of inhibitor needed to inhibit planktonic growth by 50%.
$^c$~: The $B(IC)_{50}$ values could not be accurately calculated due to the steepness of the curve.
Compounds that have a biofilm-specific activity ($2 \times BIC_{50} < IC_{50}$) are marked with asterisks (*).

Example 4. Comparison of Anti-Biofilm Activity and Toxicity of Diverse 5-Ar-2AIs Overall, it can be concluded from the results above that the N1-substituted 5-Ar-2AI 2 shows the broadest activity spectrum, with strong activity against most monospecies bacterial biofilms, the monospecies C. albicans biofilm, both the mixture of Gram-negative and the mixture of Gram-positive bacteria and against all mixed bacterial-fungal biofilms. Also the other N1-substituted compound 1 shows activity against most of these biofilms, be it at higher doses. Unfortunately, as previously reported, compound 2, and the N1-substituted 5-Ar-2AIs in general, show a strong toxicity against eukaryotic tumor cell lines, bone cells and the nematode Caenorhabditis elegans. Indeed, the N1-substituted 5-Ar-2AIs generally have a therapeutic index (TI) smaller than 1 with regard to biofilm inhibition [29]. TI is calculated as the ratio of the compound concentration producing toxicity against tumor cell lines (ICso) to the concentration needed to exert the desired 'therapeutic' effect on biofilms ($BIC_{50}$). The higher the therapeutic index, the broader the safety window of the compound. The 2N-substituted 2-aminoimidazoles 3-5 on the other hand have a good activity against most monospecies and mixed species biofilms of Gram-negatives, but have a more moderate activity against the monospecies biofilms of the Gram-positives and C. albicans and against their mixed biofilms. However, the 2N-substituted 5-Ar-2AIs, generally have a much lower toxicity, with TI far above 1 [29]. The 2-aminoimidazole/triazole conjugate 6 generally has a higher toxicity [29], and a narrow activity spectrum against monospecies bacterial biofilms. From this analysis it is clear that

Example 5. Preventive Activity of Novel Compounds Against Monospecies Bacterial and Fungal Biofilms The preventive activity of the novel N1-,2N-disubstituted 5-Ar-2AIs was first evaluated against a panel of monospecies bacterial and fungal biofilms. Interestingly, as indicated in Table 4, all compounds inhibited biofilm formation of the Gram-positive S. aureus ATCC6538 (37° C.) at low concentrations ($BIC_{50}$ between 1 and 41 µM), except for compound 8d which had a higher $BIC_{50}$ of 116 µM. Hence, these novel compounds are characterized by increased anti-biofilm activity as compared to the 5-Ar-2AIs 3 and 5 that are only substituted at the 2N-position. Bacterial growth was not affected by these compounds for concentrations equal to the $BIC_{50}$, except in case of compound 8a, pointing to biofilm-specific activity.

However, none of the compounds was active against P. aeruginosa biofilms at 25° C. or 37° C., whereas the effect on E. coli biofilm formation was strongly dependent on the substitution pattern of the 5-aryl ring. Only compounds 8a, 8b, 8e and 8f bearing an unsubstituted phenyl ring or para-chlorphenyl at the 5-position of the 2-aminoimidazole ring had a potent activity against E. coli biofilm cells at 25° C., and only compounds 8a and 8e with an unsubstituted 5-phenyl ring showed activity at 37° C. The activities at 25° C. were biofilm-specific (except in case of compound 8a), while at 37° C. also the planktonic growth was affected.

Most of the novel compounds showed a potent preventive activity against *C. albicans* biofilms with $BIC_{50}$ values between 9 and 22 μM. Only compounds 8c, 8d and 8h were not active at the highest concentration tested (100 μM). In conclusion, whereas these novel compounds gained in activity against the Gram-positive bacterium *S. aureus* compared to the previously described 2N-substituted compounds, their activity against the Gram-negative bacteria *P. aeruginosa* and *E. coli* was reduced.

TABLE 4

Effect of novel 5-Ar-2Als on a panel of monospecies biofilms of bacteria and fungi.

*S. aureus* ATCC6538 37° C.

| compd | $BIC_{50}^a$ (μm) | 95% confidence interval for $BIC_{50}$ | $IC_{50}^b$ (μm) | 95% confidence interval for $IC_{50}$ |
|---|---|---|---|---|
| 8a | ~22.9$^c$ |  | 17.9 | 15.3-21.0 |
| 8b | 5.8* | 2.5-13.5 | 9.3 | 8.3-10.3 |
| 8c | 41.0* | 2.1-400.0 | 172.7 | 151.1-197.3 |
| 8d | 116.0* | 21.6-400.0 | >400.0 |  |
| 8e | 1.0* | 0.5-1.7 | 46.5 | 24.1-89.8 |
| 8f | 6.7* | 3.2-13.8 | ~24.1 |  |
| 8g | 8.5* | 3.3-22.0 | 19.1 | 16.1-22.6 |
| 8h | 3.8* | 1.5-9.8 | 19.5 | 14.4-26.6 |

*P. aeruginosa* PA14

| | 25° C. | | | | 37° C. | | | |
|---|---|---|---|---|---|---|---|---|
| compd | $BIC_{50}^a$ (μm) | 95% confidence interval for $BIC_{50}$ | $IC_{50}^b$ (μm) | 95% confidence interval for $IC_{50}$ | $BIC_{50}^a$ (μm) | 95% confidence interval for $BIC_{50}$ | $IC_{50}^b$ (μm) | 95% confidence interval for $IC_{50}$ |
| 8a | >400.0 |  | 75.3 | 46.9-121.1 | >400.0 |  | 66.0 | 46.9-92.8 |
| 8b | >400.0 |  | 222.5 | 143.6-344.8 | >400.0 |  | 115.1 | 89.0-149.0 |
| 8c | >400.0 |  | >400.0 |  | >400.0 |  | 344.7 | 282.2-400.0 |
| 8d | >400.0 |  | >400.0 |  | >400.0 |  | >400.0 |  |
| 8e | >400.0 |  | 62.9* | 47.9-82.5 | >400.0 |  | 167.3 | 110.8-252.6 |
| 8f | >400.0 |  | >400.0 |  | >400.0 |  | >400.0 |  |
| 8g | >400.0 |  | >400.0 |  | >400.0 |  | >400.0 |  |
| 8h | >400.0 |  | >400.0 |  | >400.0 |  | >400.0 |  |

*E. coli* TG1

| | 25° C. | | | | 37° C. | | | |
|---|---|---|---|---|---|---|---|---|
| compd | $BIC_{50}^a$ (μm) | 95% confidence interval for $BIC_{50}$ | $IC_{50}^b$ (μm) | 95% confidence interval for $IC_{50}$ | $BIC_{50}^a$ (μm) | 95% confidence interval for $BIC_{50}$ | $IC_{50}^b$ (μm) | 95% confidence interval for $IC_{50}$ |
| 8a | ~47.2 |  | 51.2 | 29.1-90.2 | 41.2 | 25.3-67.0 | 10.2 | 4.4-23.9 |
| 8b | 29.5* | 15.7-55.4 | 91.9 | 33.5-252.1 | 329.9 | 161.9-400.0 | 6.1 | 3.5-10.8 |
| 8c | >400.0 |  | 150.0 | 84.8-265.2 | >400.0 |  | 74.1 | 21.8-252.4 |
| 8d | >400.0 |  | 255.2 | 194.1-335.5 | >400.0 |  | 46.3 | 25.8-83.2 |
| 8e | ~26.7* |  | 188.9 | 105.7-337.5 | ~27.6 |  | 10.5 | 6.2-17.7 |
| 8f | 29.1* | 18.1-46.9 | >400.0 |  | 305.9 | 94.2-400.0 | 370.2 | 39.2-400.0 |
| 8g | 43.0* | 10.8-170.7 | >400.0 |  | >400.0 |  | 236.6 | 108.4-400.0 |
| 8h | >400.0 |  | >400.0 |  | >400.0 |  | >400.0 |  |

*C. albicans* SC5314 37° C.

| compd | $BIC_{50}^a$ (μm) | 95% confidence interval for $BIC_{50}$ |
|---|---|---|
| 8a | 9.3 | 7.5-11.7 |
| 8b | 11.0 | 8.2-14.7 |

TABLE 4-continued

Effect of novel 5-Ar-2AIs on a panel of monospecies biofilms of bacteria and fungi.

| | | |
|---|---|---|
| 8c | >100.0 | |
| 8d | >100.0 | |
| 8e | ~11.9 | |
| 8f | 8.9 | 7.1-11.2 |
| 8g | 21.1 | 16.2-27.4 |
| 8h | >100.0 | |

$^{a}$BIC$_{50}$: concentration of inhibitor needed to inhibit biofilm formation by 50%.
$^{b}$IC$_{50}$: concentration of inhibitor needed to inhibit planktonic growth by 50%.
$^{c}$~: The B(IC)$_{50}$ values could not be accurately calculated due to the steepness of the curve.
Compounds that have a biofilm-specific activity (2 × BIC$_{50}$ < IC$_{50}$) are marked with asterisks (*).

Example 6. Preventive Activity of Novel Compounds Against Mixed Species Biofilms Finally, the preventive activity of the novel N1-,2N-disubstituted 5-Ar-2AIs was evaluated against a panel of mixed species bacterial biofilms and mixed bacterial-fungal biofilms (Table 5). Most compounds strongly inhibited both *S. epidermidis* and *C. albicans* in the *C. albicans*/*S. epidermidis* mixture, except for compounds 8c and 8d which only reduced *C. albicans*. All the novel compounds also showed a very strong, biofilm-specific effect on the *S. aureus*/*S. epidermidis* mixed biofilm, except for compound 8d. The mixed biofilm of the Gram-negative bacteria *P. aeruginosa*/*E. coli* on the other hand was only strongly inhibited by compound 8a, and at higher concentrations by compounds 8e and 8f. In agreement with the monospecies biofilm assays, these novel compounds generally showed a very strong activity against the Gram-positive bacteria and *C. albicans* in the mixed biofilms, however, they had only poor activity against the Gram-negative bacteria.

TABLE 5

Effect of novel 5-Ar-2AIs on a panel of mixed species biofilms

| | *C. albicans* SC5314 + *S. epidermidis* CFUs % survival | | | |
|---|---|---|---|---|
| | 25 μM | | 100 μM | |
| compd | C.a. | S.e. | C.a. | S.e. |
| 8a | 62.4 | 1541.7 | 1.0 | 1.0 |
| 8b | 2.0 | 6.1 | 18.2 | 0.7 |
| 8c | 3.2 | 637.0 | 8.4 | 965.7 |
| 8d | 2.5 | 1763.9 | 1.4 | 1277.8 |
| 8e | 10.0 | 93.1 | 2.5 | 0.0 |
| 8f | 2.9 | 2.5 | 7.2 | 0.3 |
| 8g | 3.3 | 0.0 | 5.9 | 0.0 |
| 8h | 6.7 | 2.0 | 3.5 | 2.2 |

| | *S. aureus* ATCC6538 + *S. epidermidis* 37° C. | | | | *E. coli* TG1 + *P. aeruginosa* PA14 37° C. | | | |
|---|---|---|---|---|---|---|---|---|
| Compd | BIC$_{50}$$^{a}$ (μm) | 95% confidence interval for BIC$_{50}$ | IC$_{50}$$^{b}$ (μm) | 95% confidence interval for IC$_{50}$ | BIC$_{50}$ (μm) | 95% confidence interval for BIC$_{50}$ | IC$_{50}$ (μm) | 95% confidence interval for IC$_{50}$ |
| 8a | 0.0* | 0.0-0.3 | ~26.1$^{c}$ | | 6.6* | 2.3-19.2 | >400.0 | |
| 8b | 1.1* | 0.7-1.7 | ~22.2 | | >400.0 | | >400.0 | |
| 8c | 5.0* | 2.9-8.5 | >400.0 | | >400.0 | | >400.0 | |
| 8d | >400.0 | | >400.0 | | >400.0 | | >400.0 | |
| 8e | ~3.0* | | ~23.6 | | 100.7* | 7.5-400.0 | >400.0 | |
| 8f | 2.0* | 1.1-3.5 | ~22.5 | | 399.6 | 26.9-400.0 | >400.0 | |
| 8g | ~5.6* | | 15.5 | 9.9-24.4 | >400.0 | | >400.0 | |
| 8h | 4.9* | 2.9-8.2 | ~25.1 | | >400.0 | | >400.0 | |

C.a.: *Candida albicans*;
S.e.: *Staphylococcus epidermidis*.
$^{a}$BIC$_{50}$: concentration of inhibitor needed to inhibit biofilm formation by 50%.
$^{b}$IC$_{50}$: concentration of inhibitor needed to inhibit planktonic growth by 50%.
$^{c}$~: The B(IC)$_{50}$ values could not be accurately calculated due to the steepness of the curve.
Compounds that have a biofilm-specific activity (2 × BIC$_{50}$ < IC$_{50}$) are marked with asterisks (*).

Example 7. Effect of Novel Compounds on Viability and Functional Behaviour of Bone Cells The novel compounds have an interesting activity profile for application in anti-biofilm coatings for orthopedic implants. Moreover, preliminary experiments indicated that these compounds retain their activity after covalent attachment to a surface, making them suitable for incorporation in both covalent anti-biofilm coatings and slow release coatings. In light of applying these compounds as anti-infective coatings on orthopedic implants, we determined their effect on viability and functional behaviour of bone cells. Additionally, this allows an easy comparison with the toxicity of the previously described 5-Ar-2AIs, which has been evaluated using the same assays [29].

The effect of the novel compounds was first tested on the viability (i.e. percentage of viable cells in treated sample compared to total number (viable and non-viable) of cells in treated sample) of osteoblasts (OB) and mesenchymal stem cells (MSC) in function of time. For each compound a dose of 12.5 μM was used, which is well above the $BIC_{50}$ value of most compounds for $S.$ $aureus$ and $S.$ $aureus/S.$ $epidermidis$ biofilm inhibition. As shown in FIG. 3A and FIG. 3B, the cell viability measured by trypan blue staining was only very slightly reduced (<10%) early in the treatment for a limited number of compounds. After 6 days of exposure none of the compounds altered the cell viability of the two cell types, except for compound 8c which very slightly reduced viability of OB. MIT staining indicated that the metabolic activity of both cell types was even increased as compared to the solvent control after 6 days treatment with compounds 8c, 8d, 8g and 8h (FIG. 4), all bearing a para-bromophenyl or 3,4-dichlorophenyl substituent at the 5-position of the imidazole ring. Interestingly, also an increase in proliferation (FIG. 3A and FIG. 3B) was observed after 6 days exposure to compounds 8c, 8d, 8g and 8h (OB, FIG. 3B) and 8d (MSC, FIG. 3A). The proliferation of MSC and OB was however slightly reduced after 6 days treatment with compounds 8a, 8e, 8f and 8g and compounds 8a and 8e respectively.

Figure 5:
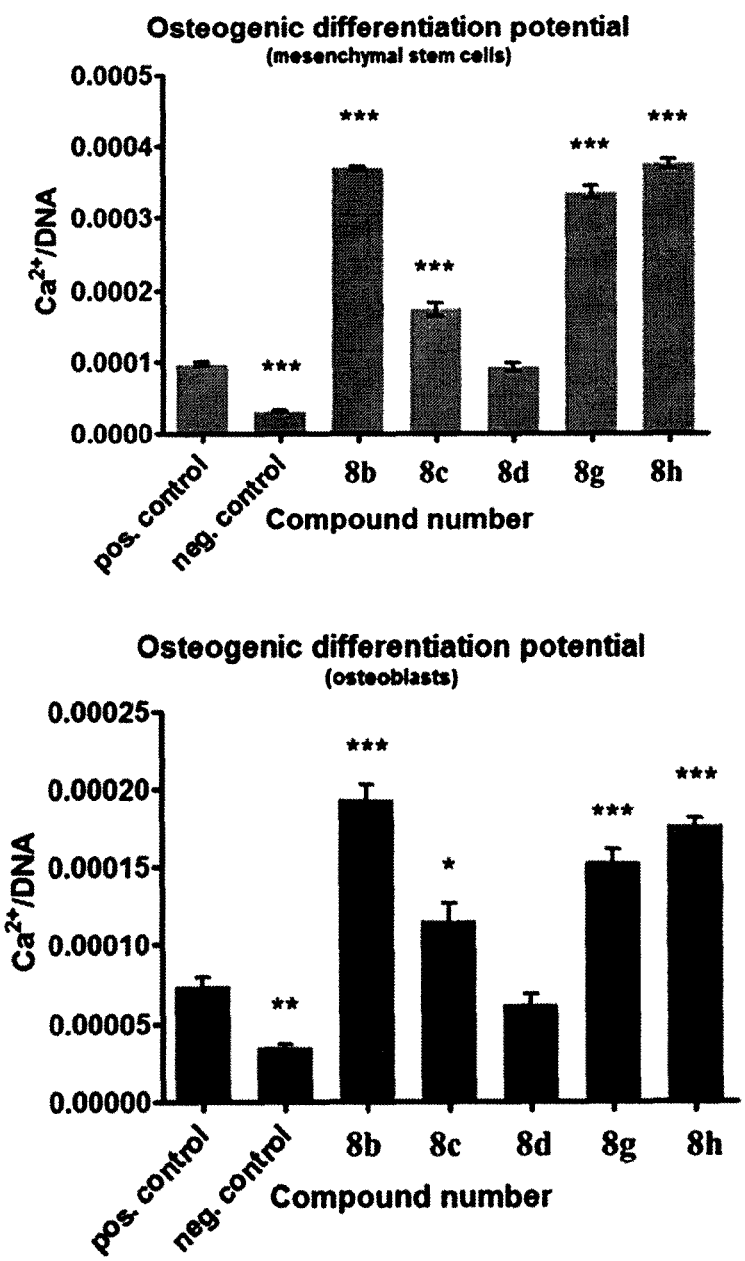
FIG. 5 Effect of selected compounds (12.5 µM) on the osteogenic differentiation potential of osteoblasts (OB) and mesenchymal stem cells (MSC) after resp. 3 and 5 weeks of exposure, as determined by measuring the amount of calcium content which was normalized by the DNA values. Bars and error bars represent resp. means and standard errors of at least four repeats. The negative control contains no osteogenic supplements. The solvent (positive) control contains osteogenic supplements and a 0.5% ethanol background. Significant differences ($p<0.05=*$; $p<0.01=$ and $p<0.001=*$) with the solvent control are indicated.

Next, compounds 8b, 8c, 8d, 8g and 8h, which allowed survival of MSC and OB cells for more than 3 weeks, were tested with respect to their osteogenic differentiation potential as those two cell types are responsible for the production of new bone matrix within bone tissue. Calcium deposition was chosen as an indicator of the osteogenic phenotype, as it is the final and functional marker of osteoblast differentiation. As shown in FIG. 5, none of the compounds negatively affected the calcium deposition of either of the two cell types at 12.5 μM. Interestingly, all compounds except compound 8d significantly ($p<0.05$ for compound 8c OB cells; $p<0.001$ for the rest of the compounds) induced the calcium deposition of both cell types. This indicates that anti-biofilm coating of orthopedic implants with these compounds might even stimulate the osseointegrative potential.

Example 8. In Vitro Anti-Biofilm Activity of LC0024-Ti Discs Against $S.$ $aureus$ The titanium discs coated with LC0024 or compound 8g from FIG. 2 showed a reduction of $S.$ $aureus$ SH1000 biofilm cells present on the surface of the discs. Biofilm formation of the $S.$ $aureus$ cells on the coated discs was 3 times lower (inhibited with 67.4%) as compared to the control discs (FIG. 7).

Example 9. In Vitro Microscopic Analysis of Smooth LC0024-Ti Discs with CLSM

Figure 8:
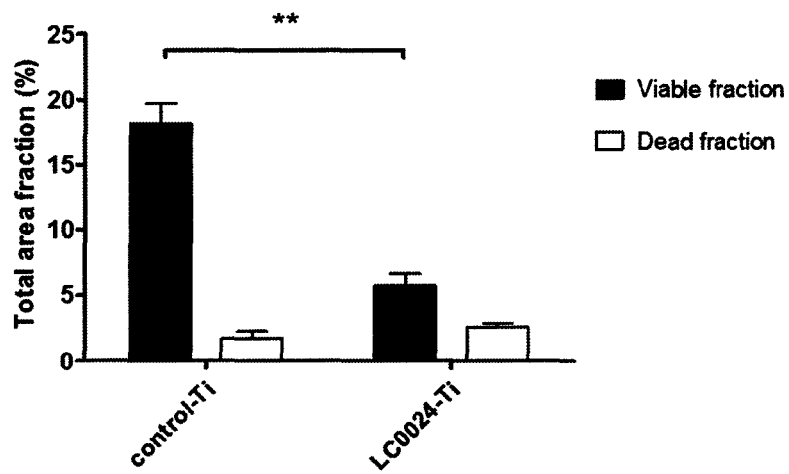
FIG. 8 CLSM analysis of S. aureus biofilms on LC0024-Ti discs. The total area fraction of S. aureus SH1000 covering the Ti-discs, divided in fraction of dead and viable cells, respectively. Means and standard errors of at least 3 repeats are shown; the area fraction calculated for each repeat is the mean value of 25 images analyzed by Mathlab (** $P<0.01$).
Figure 9:
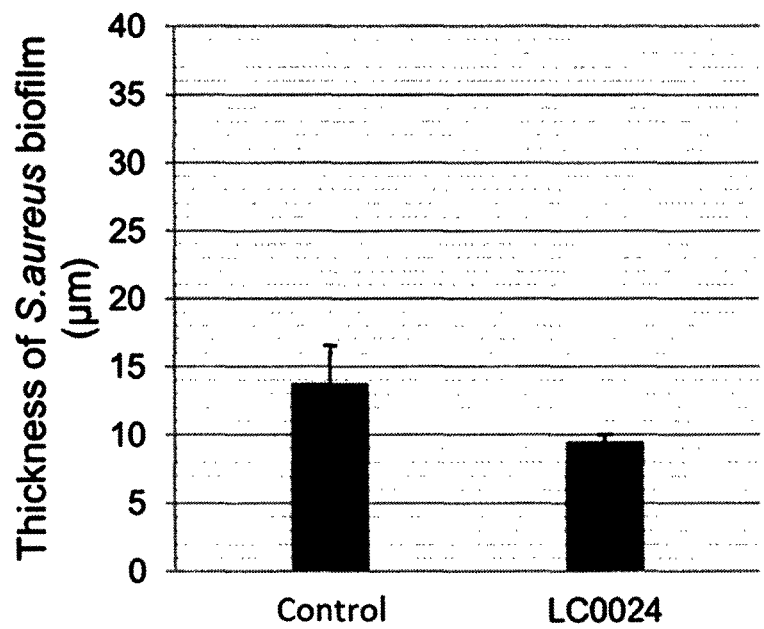
FIG. 9 The thickness of S. aureus SH1000 biofilms (µm) on LC0024-Ti versus control-Ti discs (means and standard deviations of 2 repeats are shown).

To confirm the results of the CFU count, biofilm growth on control-Ti and LC0024-Ti discs was visualized by CLSM using the LIVE/DEAD® BacLight™ stain, causing viable cells to turn green and dead cells to color red. CSLM imaging showed a significant reduction of viable (green) biofilm cells on the LC0024-Ti discs compared to the untreated control-Ti discs (FIG. 8). Further image analysis confirmed this reduction since the area fraction on the LC0024-Ti discs covered with viable $S.$ $aureus$ was 3 times ($P<0.01$) lower compared to the untreated control-Ti discs (31% viable cells left) (FIG. 8). FIG. 9 shows that the thickness of the biofilm on the coated discs was only 5 μm smaller than the control sample.

Example 10. In Vivo Anti-Biofilm Effect of Smooth Titanium Discs Coated with Compound LC0024 (Compound 8g from FIG. 2)

Figure 10:
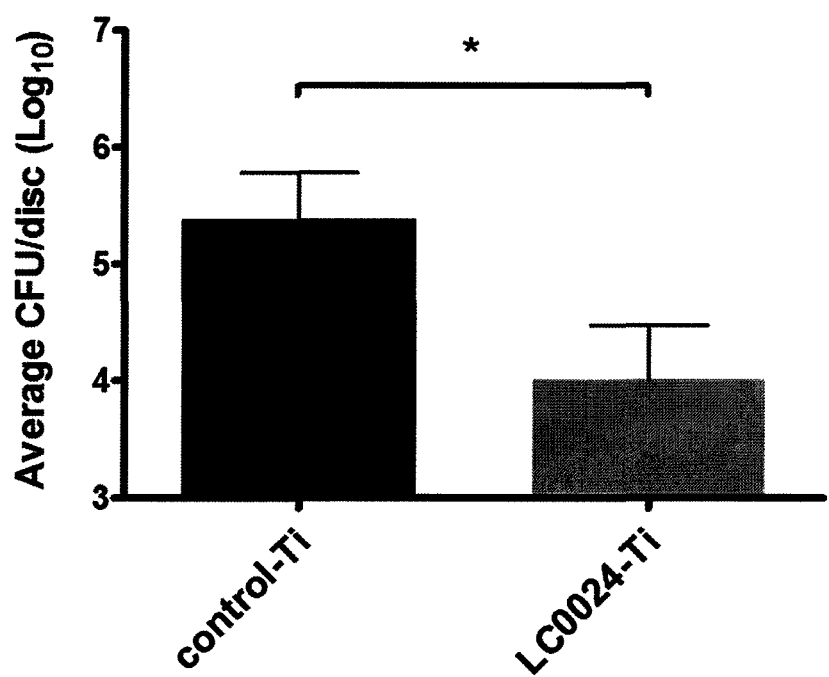
FIG. 10 S. aureus SH1000 recovery of control-Ti and LC0024-Ti discs. CFUs are represented as $\log_{10}$ values per individual disc (means and SEM of 2 independent experiments are shown; * $P<0.05$).

The in vivo anti-biofilm activity of the LC0024-coated Ti discs was evaluated using an adapted model of biomaterial-associated infection, which was originally developed to study $S.$ $epidermidis$ biofilm formation on Ti and silicone substrates (31). Hereto, control-Ti and LC0024-Ti discs were implanted subcutaneously in the back of the mice, and 24 h later ~$10^8$ $S.$ $aureus$ cells were subcutaneously injected alongside the implants to allow in vivo biofilm formation. After 4 days, the discs were explanted and biofilm formation on the Ti discs was evaluated by CFU counts. As shown in FIG. 10, the average recovery of $S.$ $aureus$ cells was 24 times lower for the LC0024-coated discs than for the uncoated control discs. This significant ($p<0.05$) decrease indicates the effectiveness of the smooth LC0024-Ti discs for in vivo applications.

Example 11. Cytotoxicity of Human Bone Marrow Derived Stromal Cells on Coated Titanium Discs Titanium discs were coated with compound 8g (or LC0024). FIG. 11 shows that cell culture morphology of the human bone marrow derived stromal cells remained unchanged upon usage of coated titanium discs. Further no zone of growth inhibition was observed for all discs tested. According to the direct contact test, all discs/coated molecules are considered non-cytotoxic.

Example 12. In Vitro Osseointegration Potential

Figure 12:
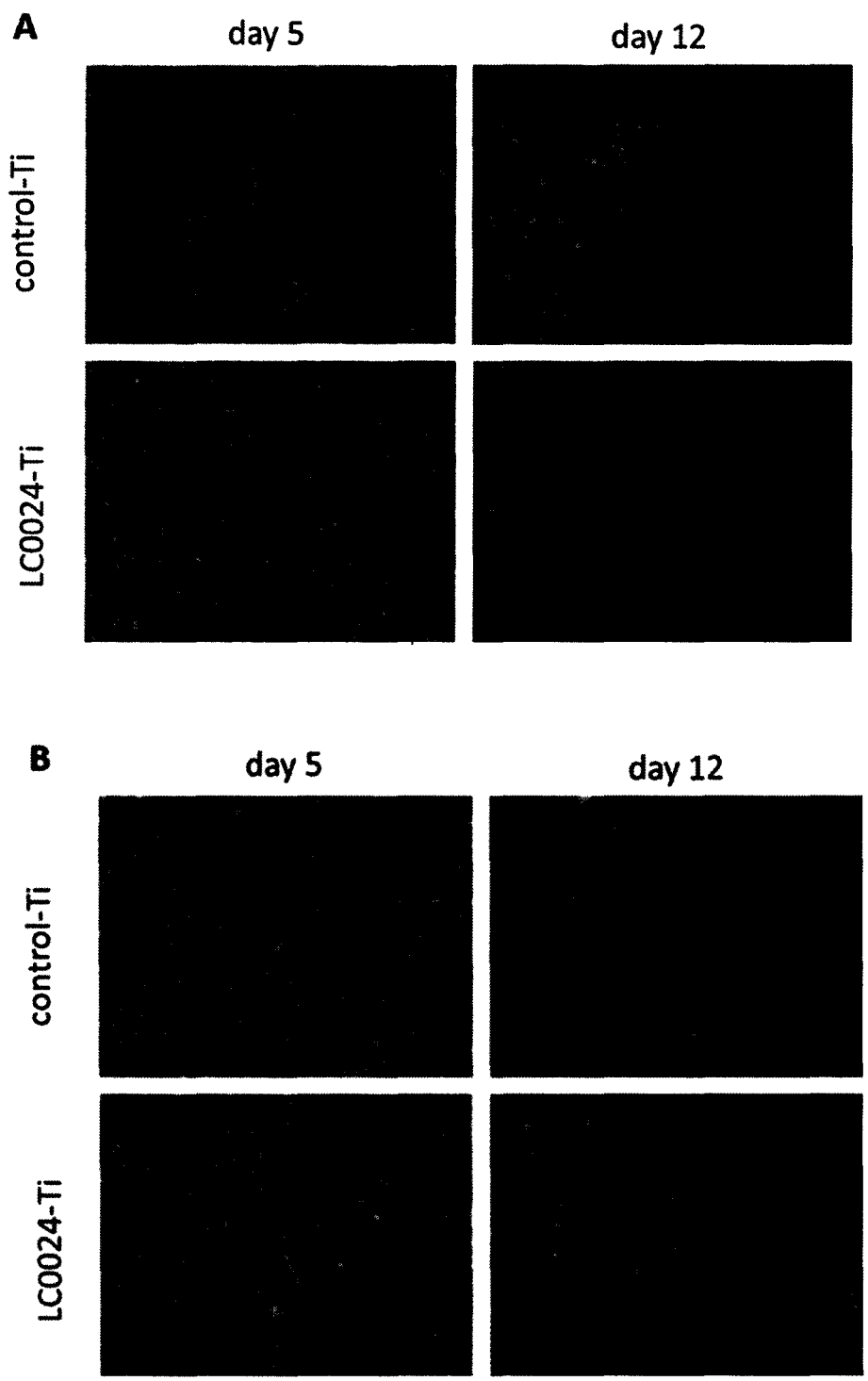
FIG. 12 Phalloidin/DAPI stain of (A) human bone marrow derived stromal cells and (B) human microvascular endothelial cells seeded on control-Ti and LC0024-Ti discs and cultured for 5 and 12 days.

An important issue for application of implants is the effect on osteogenic (MSC) and vasculogenic (HMVEC) cells. These cell types are necessary for the integration of the implant in the surrounding tissue, i.e. osseointegration (32). As observed by Phalloidin/DAPI stain at day 5 (FIG. 12), the tested control-Ti and LC0024-Ti discs supported attachment and growth of MSC and HMVEC. Moreover, the surface of the discs enabled growth of both cell types also for extended periods of time, i.e. 12 days. For all discs tested, obvious increase in cell numbers was observed at day 12 in comparison to day 5.

Taken together, all discs tested supported attachment and growth of osteogenic and vasculogenic cells, indicating good osseointegration potential. Generally, MSC performed better than HMVEC; they attached on more substrate types and proliferated more, which is expected due to differences in characteristics between the cell types.

REFERENCES

1. Bjarnsholt T, Tolker-Nielsen T, Hoiby N, Givskov M. 2010. Interference of $Pseudomonas$ $aeruginosa$ signalling and biofilm formation for infection control. Expert Rev Mol Med 12:e11.

2. Landini P, Antoniani D, Burgess J G, Nijland R. 2010. Molecular mechanisms of compounds affecting bacterial biofilm formation and dispersal. Appl Microbiol Biotechnol 86:813-823.
3. Lynch A S, Abbanat D. 2010. New antibiotic agents and approaches to treat biofilm-associated infections. Expert Opin Ther Pat 20:1373-1387.
4. Ren D, Zuo R, Gonzalez Barrios A F, Bedzyk L A, Eldridge G R, Pasmore M E, Wood T K. 2005. Differential gene expression for investigation of *Escherichia coli* biofilm inhibition by plant extract ursolic acid. Appl Environ Microbiol 71:4022-4034.
5. Rogers Sa, Huigens R W, Melander C. 2009. A 2-aminobenzimidazole that inhibits and disperses gram-positive biofilms through a zinc-dependent mechanism. Journal of the American Chemical Society 131:9868-9869.
6. Steenackers H, Ermolat'ev D S, Savaliya B, De Weerdt A, De Coster D, Van der Eycken E, De Vos D, Vanderleyden J, De Keersmaecker S C. 2010. Structure Activity Relationship of 4(5)-Phenyl-2-amino-1H-imidazoles, N1-Substituted 2-Aminoimidazoles and Imidazo[1,2-a]pyrimidinium Salts as Inhibitors of the Biofilm Formation by *Salmonella Typhimurium* and *Pseudomonas aeruginosa*. Journal of Medicinal Chemistry 54:472-482.
7. Steenackers H P, Ermolat'ev D S, Savaliya B, Weerdt A D, Coster D D, Shah A, Van der Eycken E V, De Vos D E, Vanderleyden J, De Keersmaecker S C. 2011. Structure-activity relationship of 2-hydroxy-2-aryl-2,3-dihydroimidazo[1,2-a]pyrimidinium salts and 2N-substituted 4(5)-aryl-2-amino-1H-imidazoles as inhibitors of biofilm formation by *Salmonella Typhimurium* and *Pseudomonas aeruginosa*. Bioorg Med Chem 19:3462-3473.
8. Ermolat'ev D S, Bariwal J B, Steenackers H P, De Keersmaecker S C, Van der Eycken E V. 2010. Concise and diversity-oriented route toward polysubstituted 2-aminoimidazole alkaloids and their analogues. Angew Chem Int Ed Engl 49:9465-9468.
9. Steenackers H, Ermolat'ev D, Trang T, Savalia B, De Weerdt A, Shah A, Vanderleyden J, Van der Eycken E. 2013. Microwave-Assisted One-Pot Synthesis and Anti-Biofilm Activity of 2-Amino-1H-imidazole/Triazole Conjugates. Organic and Biomolecular Chemistry Submitted.
10. Folkesson A, Jelsbak L, Yang L, Johansen H K, Ciofu O, Hoiby N, Molin S. 2012. Adaptation of *Pseudomonas aeruginosa* to the cystic fibrosis airway: an evolutionary perspective. Nat Rev Microbiol 10:841-851.
11. Guo X, Chen W, Chen B, Huang W, Qi W, Zhang G, Yu Y. 2015. One-Pot Three-Component Strategy for Functionalized 2-Aminoimidazoles via Ring Opening of α-Nitro Epoxides. Organic letters 17:1157-1159.
12. Ermolat'ev D S, Babaev E V, Van der Eycken E V. 2006. Efficient one-pot, two-step, microwave-assisted procedure for the synthesis of polysubstituted 2-aminoimidazoles. Organic letters 8:5781-5784.
13. Steenackers H, Ermolat'ev D, Trang T T, Savalia B, Sharma U K, De Weerdt A, Shah A, Vanderleyden J, Van der Eycken E V. 2014. Microwave-assisted one-pot synthesis and anti-biofilm activity of 2-amino-1H-imidazole/triazole conjugates. Org Biomol Chem 12:3671-3678.
14. Giles R L, Sullivan J D, Steiner A M, Looper R E. 2009. Addition-Hydroamination Reactions of Propargyl Cyanamides: Rapid Access to Highly Substituted 2-Aminoimidazoles. Angewandte Chemie (International ed in English) 121:3162-3166.
15. Liberati N T, Urbach J M, Miyata S, Lee D G, Drenkard E, Wu G, Villanueva J, Wei T, Ausubel F M. 2006. An ordered, nonredundant library of *Pseudomonas aeruginosa* strain PA14 transposon insertion mutants. Proc Natl Acad Sci USA 103:2833-2838.
16. Sambrook J, Fritsch E F, Maniatis T. 1989. Molecular cloning: a laboratory manual, 2nd ed. Cold Spring Harbor Laboratory Press, Cold Spring Harbor, N.Y.
17. Blattner F, Plunkett G I, Bloch C, Perna N, Burland V, Riley M, Collado-Vides J, Glasner J, Rode C, Mayhew G, Gregor J, Davis N, Kirkpatrick H, Goeden M, Rose D, Mau B, Shao Y. 1997. The Complete Genome Sequence of *Escherichia coli* K-12. Science 277:1453-1462.
18. Fields P I, Swanson R V, Haidaris C G, Heffron F. 1986. Mutants of *Salmonella typhimurium* that cannot survive within the macrophage are avirulent. Proc Natl Acad Sci USA 83:5189-5193.
19. Andersen J B, Heydorn A, Hentzer M, Eberl L, Geisenberger O, Christensen B B, Molin S, Givskov M. 2001. gfp-based N-acyl homoserine-lactone sensor systems for detection of bacterial communication. Appl Environ Microbiol 67:575-585.
20. Palleroni N J, Holmes B. 1981. *Pseudomonas cepacia* sp. nov., nom. rev. International Journal of Systematic Bacteriology 31:479-481.
21. Fonzi W A, Irwin M Y. 1993. Isogenic Strain Construction and Gene Mapping in *Candida albicans*. Genetics 134:717-728.
22. O'Neill A J. 2010. *Staphylococcus aureus* SH1000 and 8325-4: comparative genome sequences of key laboratory strains in staphylococcal research. Lett Appl Microbiol 51:358-361.
23. Horsburgh M J, Aish J L, White I J, Shaw L, Lithgow J K, Foster S J. 2002. B Modulates Virulence Determinant Expression and Stress Resistance: Characterization of a Functional rsbU Strain Derived from *Staphylococcus aureus* 8325-4. Journal of Bacteriology 184:5457-5467.
24. Delattin N, De Brucker K, Vandamme K, Meert E, Marchand A, Chaltin P, Cammue B P, Thevissen K. 2014. Repurposing as a means to increase the activity of am photericin B and caspofungin against *Candida albicans* biofilms. J Antimicrob Chemother 69:1035-1044.
25. Janssens J C, Steenackers H, Robijns S, Gellens E, Levin J, Zhao H, Hermans K, De Coster D, Verhoeven T L, Marchal K, Vanderleyden J, De Vos D E, De Keersmaecker S C. 2008. Brominated furanones inhibit biofilm formation by *Salmonella enterica* serovar *Typhimurium*. Appl Environ Microbiol 74:6639-6648.
26. O'Brien J, Wilson I, Orton T, Pognan F. 2000. Investigation of the Alamar Blue (resazurin) fluorescent dye for the assessment of mammalian cell cytotoxicity. Europan Journal of Biochemistry 267:5421-5426.
27. Steenackers H, Dubey A, Robijns S, Ermolat'ev D, Delattin N, Dovgan B, Girandon L, Frohlich M, De Brucker K, Cammue B P, Thevissen K, Balzarini J, Van der Eycken E V, Vanderleyden J. 2014. Evaluation of the Toxicity of 5-Aryl-2-Aminoimidazole-Based Biofilm Inhibitors against Eukaryotic Cell Lines, Bone Cells and the Nematode *Caenorhabditis elegans*. Molecules 19:16707-16723.
28. Robijns S C, De Pauw B, Loosen B, Marchand A, Chaltin P, De Keersmaecker S C, Vanderleyden J, Steenackers H P. 2012. Identification and characterization of 4-[4-(3-phenyl-2-propen-1-yl)-1-piperazinyl]-5H-pyrimido[5,4-b]indole derivatives as *Salmonella* biofilm inhibitors. FEMS Immunol Med Microbiol 65:390-394.
29. Mishra N M, Briers Y, Lamberigts C, Steenackers H, Robijns S, Landuyt B, Vanderleyden J, Schools L, Lavigne R, Luyten W, Van der Eycken E V. 2015. Evaluation of the antibacterial and antibiofilm activities of novel CRAMP-vancomycin conjugates with diverse linkers. Org Biomol Chem 13:7477-7486.
30. Liebens V, Gerits E, Knapen W J, Swings T, Beullens S, Steenackers H P, Robijns S, Lippell A, O'Neill A J, Veber M, Frohlich M, Krona A, Lovenklev M, Corbau R, Marchand A, Chaltin P, De Brucker K, Thevissen K, Cammue B P, Fauvart M, Verstraeten N, Michiels J. 2014. Identification and characterization of an anti-pseudomonal dichlorocarbazol derivative displaying anti-biofilm activity. Bioorg Med Chem Lett 24:5404-5408.
31. Bunders C A, Richards J J, Melander C. 2010. Identification of aryl 2-aminoimidazoles as biofilm inhibitors in Gram-negative bacteria. Bioorg Med Chem Lett 20:3797-3800.
32. Junker L M, Clardy J. 2007. High-throughput screens for small-molecule inhibitors of *Pseudomonas aeruginosa* biofilm development. Antimicrob Agents Chemother 51:3582-3590.
33. Zeng Z, Qian L, Cao L, Tan H, Huang Y, Xue X, Shen Y, Zhou S. 2008. Virtual screening for novel quorum sensing inhibitors to eradicate biofilm formation of *Pseudomonas aeruginosa*. Appl Microbiol Biotechnol 79:119-126.
34. Cao Y, Dai B, Wang Y, Huang S, Xu Y, Gao P, Zhu Z, Jiang Y. 2008. In vitro activity of baicalein against *Candida albicans* biofilms. Int J Antimicrob Agents 32:73-77.
35. Yang L, Rybtke M T, Jakobsen T H, Hentzer M, Bjarnsholt T, Givskov M, Tolker-Nielsen T. 2009. Computer-aided identification of recognized drugs as *Pseudomonas aeruginosa* quorum-sensing inhibitors. Antimicrob Agents Chemother 53:2432-2443.
36. Payne D E, Martin N R, Parzych K R, Rickard A H, Underwood A, Boles B R. 2013. Tannic acid inhibits *Staphylococcus aureus* surface colonization in an isaA-dependent manner. Infection and Immunity 81:496-504.
37. Hancock V, Dahl M, Vejborg R M, Klemm P. 2010. Dietary plant components ellagic acid and tannic acid inhibit *Escherichia coli* biofilm formation. J Med Microbiol 59:496-498.
38. Rogers S A, Bero J D, Melander C. 2010. Chemical synthesis and biological screening of 2-aminoimidazole-based bacterial and fungal antibiofilm agents. Chembiochem 11:396-410.
39. Steenackers H P, Ermolat'ev D S, Savaliya B, De Weerdt A, De Coster D, Shah A, Van der Eycken E V, De Vos D E, Vanderleyden J, De Keersmaecker S C. 2011. Structure-activity relationship of 4(5)-aryl-2-amino-1H-imidazoles, N1-substituted 2-aminoimidazoles and imidazo[1,2-a]pyrimidinium salts as inhibitors of biofilm formation by *Salmonella typhimurium* and *Pseudomonas aeruginosa*. J Med Chem 54:472-484.
40. Tournu H, Van Dijck P. 2012. *Candida* biofilms and the host: models and new concepts for eradication. Int J Microbiol 2012:845352.
41. Burmolle M, Ren D, Bjarnsholt T, Sorensen Si. 2014. Interactions in multispecies biofilms: do they actually matter? Trends Microbiol 22:84-91.
42. Lee K W, Periasamy S, Mukherjee M, Xie C, Kjelleberg 5, Rice S A. 2014. Biofilm development and enhanced stress resistance of a model, mixed-species community biofilm. ISME J 8:894-907.
43. Harriott M M, Noverr M C. 2009. *Candida albicans* and *Staphylococcus aureus* form polymicrobial biofilms: effects on antimicrobial resistance. Antimicrob Agents Chemother 53:3914-3922.
44. Adam B, Baillie G S, Douglas U. 2002. Mixed species biofilms of *Candida albicans* and *Staphylococcus epidermidis*. J Med Microbiol 51:344-349.
45. Luppens S B I, Kara D, Bandounas L, Jonker M J, Wittink F Ra, Bruning O, Breit T M, Ten Cate J M, Crielaard W. 2008. Effect of *Veillonella parvula* on the antimicrobial resistance and gene expression of *Streptococcus mutans* grown in a dual-species biofilm. Oral microbiology and immunology 23:183-189.
46. Schwering M, Song J, Louie M, Turner R J, Ceri H. 2013. Multi-species biofilms defined from drinking water microorganisms provide increased protection against chlorine disinfection. Biofouling 29:917-928.
47. Lopes S P, Ceri H, Azevedo N F, Pereira M O. 2012. Antibiotic resistance of mixed biofilms in cystic fibrosis: impact of emerging microorganisms on treatment of infection. Int J Antimicrob Agents 40:260-263.
48. Cavalcanti I M, Del Bel Cury A A, Jenkinson H F, Nobbs A H. 2016. Interactions between *Streptococcus oralis*, *Actinomyces oris*, and *Candida albicans* in the development of multispecies oral microbial biofilms on salivary pellicle. Mol Oral Microbiol doi:10.1111/omi.12154.
49. Cerqueira L, Oliveira J A, Nicolau A, Azevedo N F, Vieira M J. 2013. Biofilm formation with mixed cultures of *Pseudomonas aeruginosa/Escherichia coli* on silicone using artificial urine to mimic urinary catheters. Biofouling 29:829-840.
50. Iwase T, Uehara Y, Shinji H, Tajima A, Seo H, Takada K, Agata T, Mizunoe Y. 2010. *Staphylococcus epidermidis* Esp inhibits *Staphylococcus aureus* biofilm formation and nasal colonization. Nature 465:346-349.
51. Ribeiro M, Monteiro F J, Ferraz M P. 2012. Infection of orthopedic implants with emphasis on bacterial adhesion process and techniques used in studying bacterial-material interactions. Biomatter 2:176-194.

The invention claimed is:

1. A substituted 5-aryl-2-aminoimidazole according to formula (A):

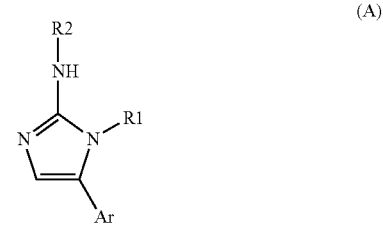

(A)

or a pharmaceutically acceptable salt, hydrate, solvate, or stereoisomer thereof, wherein:

R1 is substituted or unsubstituted $C_{4-12}$ alkyl or $C_{3-12}$ cycloalkyl;

R2 is substituted or unsubstituted $C_{2-3}$ alkyl, $C_{4-10}$ alkyl, or $C_{3-10}$ cycloalkyl; and Ar is an aryl group.

2. The substituted 5-aryl-2-aminoimidazole according to claim 1, wherein Ar is a substituted or unsubstituted aryl group selected from the group consisting of azulenyl, indanyl, indenyl, naphthyl, phenyl, and tetrahydronaphthyl.

3. A substituted 5-aryl-2-aminoimidazole represented by the structural formula (I):

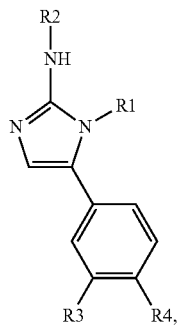

(I)

and pharmaceutically acceptable salts, hydrates, solvates, or stereoisomers thereof, wherein:

R1 is selected from the group consisting of substituted or unsubstituted $C_{4-12}$ alkyl and $C_{3-12}$ cycloalkyl;

R2 is selected from the group consisting of substituted or unsubstituted $C_{2-3}$ alkyl, $C_{4-10}$ alkyl, and $C_{3-10}$ cycloalkyl;

R3 and R4 are each independently selected from the group consisting of halogen, nitro, methoxy, methyl, hydroxyl, and methylsulfonyl.

4. A substituted 5-aryl-2-aminoimidazole compound selected from the group consisting of:
N-isobutyl-1-octyl-5-phenyl-1H-imidazol-2-amine,
5-(4-chlorophenyl)-N-isobutyl-1-octyl-1H-imidazol-2-amine,
5-(4-bromophenyl)-N-isobutyl-1-octyl-1H-imidazol-2-amine,
5-(3,4-dichlorophenyl)-N-isobutyl-1-octyl-1H-imidazol-2-amine,
N-cyclopentyl-1-octyl-5-phenyl-1H-imidazol-2-amine,
5-(4-chlorophenyl)-N-cyclopentyl-1-octyl-1H-imidazol-2-amine,
5-(4-bromophenyl)-N-cyclopentyl-1-octyl-1H-imidazol-2-amine, and
5-(3,4-dichlorophenyl)-N-cyclopentyl-1-octyl-1H-imidazol-2-amine.

5. A surface coated with the substituted 5-aryl-2-aminoimidazole according to claim 1.

6. The surface according to claim 5, wherein the surface is a surface of a veterinary or medical implant.

7. The surface according to claim 5, wherein the surface is a surface of a titanium implant.

8. The substituted 5-aryl-2-aminoimidazole according to claim 1, wherein Ar is an aryl group selected from the group consisting of phenyl, monosubstituted phenyl, and polysubstituted phenyl.

* * * * *